United States Patent
Bhyri et al.

(10) Patent No.: US 12,319,917 B2
(45) Date of Patent: Jun. 3, 2025

(54) EXPRESSION MODULATING ELEMENTS AND METHODS OF USE

(71) Applicant: PIONEER HI-BRED INTERNATIONAL, INC., Johnston, IA (US)

(72) Inventors: Priyanka Bhyri, Johnston, IA (US); Amitabh Mohanty, Hyderabad (IN); Phanikanth Turlapati, Hyderabad (IN)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 520 days.

(21) Appl. No.: 17/288,509

(22) PCT Filed: Nov. 5, 2019

(86) PCT No.: PCT/US2019/059886
§ 371 (c)(1),
(2) Date: Apr. 23, 2021

(87) PCT Pub. No.: WO2020/097092
PCT Pub. Date: May 14, 2020

(65) Prior Publication Data
US 2021/0388369 A1    Dec. 16, 2021

Related U.S. Application Data

(60) Provisional application No. 62/756,354, filed on Nov. 6, 2018.

(51) Int. Cl.
*C12N 15/82*    (2006.01)
*C07K 14/41*    (2006.01)
*C07K 14/415*   (2006.01)

(52) U.S. Cl.
CPC ........ *C12N 15/8216* (2013.01); *C07K 14/415* (2013.01)

(58) Field of Classification Search
CPC .............................................. C12N 15/8216
See application file for complete search history.

(56) References Cited

FOREIGN PATENT DOCUMENTS

| WO | WO-2012009551 A1 * | 1/2012 | ........... C07K 14/415 |
|---|---|---|---|
| WO | 2018/183878 A1 | 10/2018 | |

OTHER PUBLICATIONS

Guiltinan et al., 1990, A plant leucine zipper protein that recognizes an abscisic acid response element. Science, 250(4978), 267-271. (Year: 1990).*
Simpson et al., 2003, Two different novel cis-acting elements of erd1, a clpA homologous *Arabidopsis* gene function in induction by dehydration stress and dark-induced senescence. The Plant Journal, 33(2), 259-270. (Year: 2003).*
Chen et al., 2018, Enhanced vascular activity of a new chimeric promoter containing the full CaMV 35S promoter and the plant Xylogen Protein 1 promoter. 3 Biotech, 8, 1-9. (Year: 2018).*
Symmons et al., 2013, From remote enhancers to gene regulation: charting the genome's regulatory landscapes. Philosophical Transactions of the Royal Society B: Biological Sciences, 368(1620), 20120358. (Year: 2013).*
Weber et al., 2016, Plant enhancers: a call for discovery. Trends in plant science, 21(11), 974-987. (Year: 2016).*
Narusaka et al., 2003, Interaction between two cis-acting elements, ABRE and DRE, in ABA-dependent expression of *Arabidopsis* rd29A gene in response to dehydration and high-salinity stresses. The Plant Journal, 34(2), 137-148. (Year: 2003).*
Simpson et al., 2003, Two different novel cis-acting elements of erd1, a clpA homologous *Arabidopsis* gene function in induction by dehydration stress and dark-induced senescence. The Plant Journal, 33(2), 259-270. (previously presented) (Year: 2003).*
Zhang et al., 2005, Cis-regulatory element based targeted gene finding: genome-wide identification of abscisic acid-and abiotic stress-responsive genes in *Arabidopsis thaliana*. Bioinformatics, 21(14), 3074-3081. (Year: 2005).*
Hobo et al., 1999, ACGT-containing abscisic acid response element (ABRE) and coupling element 3 (CE3) are functionally equivalent. The Plant Journal, 19(6), 679-689. (Year: 1999).*
International Search Report and Written Opinion for International Application No. PCT/US2019/059886, Mailed Mar. 30, 2020.
International Preliminary Report on Patentability for International Application No. PCT/US2019/059886, mailed May 20, 2021, 9 Pages.
Lois R., et al., "A Phenylalanine Ammonia-lyase Gene From Parsley: Structure, Regulation and Identification of Elicitor and Light Responsive Cis-acting Elements," The EMBO Journal, 1989, vol. 8, No. 6, pp. 1641-1648.

* cited by examiner

*Primary Examiner* — Cathy Kingdon
*Assistant Examiner* — Santosh Sharma

(57) ABSTRACT

The disclosure relates to gene expression modulation elements from plants and their use in modulating the expression of one or more heterologous nucleic acid fragments in plants. The disclosure further discloses compositions, polynucleotide constructs, transformed host cells, plants and seeds containing the expression modulating elements, and methods using the same.

15 Claims, 1 Drawing Sheet
Specification includes a Sequence Listing.

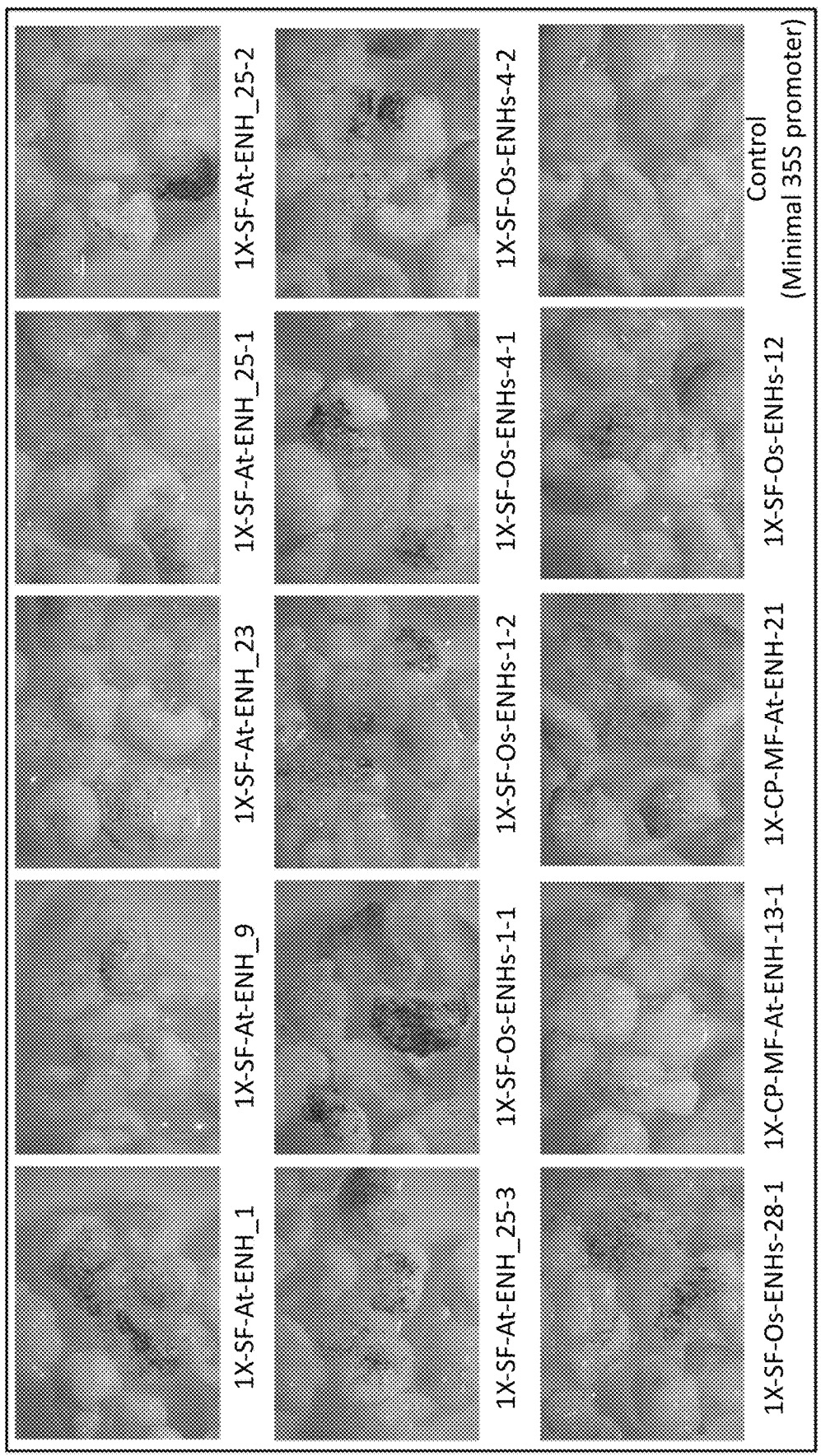

EXPRESSION MODULATING ELEMENTS AND METHODS OF USE

FIELD

This disclosure relates to a plant regulatory elements and fragments thereof and their use in altering expression of nucleotide sequences in plants.

REFERENCE TO SEQUENCE LISTING SUBMITTED ELECTRONICALLY

The official copy of the sequence listing is submitted electronically via EFS-Web as an ASCII formatted sequence listing with a file named "7828SequenceListing_ST25.txt" created on Oct. 22, 2019 and having a size of 14.7 kilobytes and is filed concurrently with the specification. The sequence listing contained in this ASCII formatted document is part of the specification and is herein incorporated by reference in its entirety.

BACKGROUND

Recent advances in plant genetic engineering have opened new doors to engineer plants to have improved characteristics or traits, such as plant disease resistance, insect resistance, herbicidal resistance, and yield improvement. Appropriate regulatory signals present in proper configurations help obtain the desired expression of a gene of interest. These regulatory signals generally include a promoter region, a 5' non-translated leader sequence, an intron, and a 3' transcription termination/polyadenylation sequence.

Expression modulating elements that increase or decrease expression of operably linked nucleotide sequences in plants are desired to modulate the expression of one or more genes of interest. This disclosure provides such expression modulation elements and methods of use.

SUMMARY

Provided is a method of modulating expression of an endogenous polynucleotide in a plant cell, the method includes altering one or more nucleotides in a regulatory region of the endogenous polynucleotide such that the regulatory region of the polynucleotide includes an expression modulating element (EME) having at least one copy of a polynucleotide sequence selected from the group consisting of SEQ ID NOS: 1-100, or a functional fragment thereof, wherein the expression modulating element is heterologous to the endogenous polynucleotide. In certain embodiments, the alteration of one or more nucleotides is by genome modification.

In certain embodiments, the EME further comprises additional copies of the expression modulating element such that about 2× to 20× copies of the EMEs are present in the regulatory region of the endogenous polynucleotide or a recombinant polynucleotide. In certain embodiments, when more than one copy of the EME is present, it can be present in one or more of the configurations selected from the group consisting of: head to head, head to tail, tail to head, tail to tail, and a combination thereof. In certain embodiments, the additional copies are contiguous. In certain embodiments, the additional copies are separated by a spacer sequence, which may include about 1 to 50 nucleotides. In certain embodiments, the EME is a combination of one or more copies of heterologous expression modulating elements.

In certain embodiments, the EME is created in the genome of plant cells by altering no more than 2, 3, 4, 5, 6, 7, 8, 9, 10, 11, 12, 13, 14 or 15 nucleotides in the regulatory region of the endogenous polynucleotide. In certain embodiments, when one or more copies of the EMEs are present, the regulatory region is created by altering no more than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 27, 38, 39 or 40 nucleotides in the regulatory region of the endogenous polynucleotide.

In certain embodiments, the EME is inserted upstream or downstream of the transcriptional start site of the endogenous polynucleotide. In certain embodiments, the EME is inserted into the regulatory region of the endogenous polynucleotide such that the expression modulating element is operably linked to the endogenous polynucleotide. In certain embodiments, the EME is inserted upstream of the endogenous promoter. In certain embodiments, the EME is inserted in the endogenous promoter region. In certain embodiments, the EME is inserted within 100 base pairs (bp) (e.g., within 90 bp, within 80 within 70 bp, within 60 bp, within 50 bp, within 40 bp, within 30 bp, within 20 bp, or within 10 bp) of the TATA box of the endogenous promoter. In certain embodiments, the expression of the endogenous polynucleotide is increased in a plant cell compared to a control plant cell not comprising the EME operably linked to the endogenous polynucleotide.

In embodiments directed to methods utilizing EMEs and compositions containing EMEs, suitable plant cell includes plant cells from monocots and dicots such as, for example, maize, rice, soybean, sunflower, wheat, canola, cotton, or sorghum. In certain embodiments, the endogenous polynucleotide is involved in drought tolerance, disease resistance, herbicide tolerance, pest resistance, yield increase, yield stability, nitrogen utilization efficiency or a combination thereof. In certain embodiments, the endogenous polynucleotide is a microRNA or a microRNA precursor.

In embodiments directed to methods utilizing EMEs and compositions containing EMEs where genome modification is involved, appropriate techniques include: a site-specific double strand break (DSB) mediated by a polynucleotide-guided endonuclease, zinc finger nuclease, a transcription activator-like effector nuclease (TALEN), polynucleotide-guided recombinase or engineered site-specific meganucleases, or Argonaute or a site-specific base edit mediated by an C·G to T·A or an A·T to G·C base editing deaminase enzymes.

In certain embodiments, the EME is operably linked to a heterologous minimal core promoter; a heterologous intron; a heterologous terminator; a heterologous promoter; a heterologous enhancer; a heterologous coding sequence; and a heterologous micro RNA sequence.

Also provided are methods of increasing expression of a polynucleotide encoding a polypeptide in a plant, the method comprising expressing the polynucleotide by operably linking the polynucleotide with an expression modulating element having at least one copy of the element selected from the group consisting of SEQ ID NOS: 1-100, or a functional fragment thereof. In certain embodiments, the expression modulating element is heterologous to the polynucleotide. In certain embodiments, the expression modulating element is heterologous to a promoter functional in the plant. In certain embodiments, the expression modulating element is heterologous to both the polynucleotide and to the promoter functional in the plant.

In certain embodiments, the polypeptide encoded by the polynucleotide (e.g., endogenous polynucleotide or heterologous nucleic acid sequence of the recombinant DNA construct) operably linked to one or more EMEs confers herbicide tolerance, insect resistance, disease resistance, abiotic stress tolerance, biotic stress tolerance, yield stability, yield increase and a combination thereof. In certain embodiments, the EME increases or decreases the expression of a polynucleotide involved in plant architecture or maturity.

Further provided are recombinant DNA constructs comprising a polynucleotide sequence comprising an expression modulating element comprising any of the sequences set forth in SEQ ID NOS: 1-100, or a functional fragment thereof, operably linked to at least one heterologous nucleic acid sequence. In certain embodiments, the heterologous nucleic acid sequence encodes a polypeptide.

Provided is a plant cell comprising an EME selected from the group consisting of SEQ ID NOS: 1-100, or a functional fragment thereof, wherein the expression modulating element is operably linked to an endogenous polynucleotide. In certain embodiments, the heterologous polynucleotide encodes a polypeptide. Also provided is a cell comprising a recombinant DNA construct that includes one or more EMEs described herein; In certain embodiments, the cell is a plant cell or a bacterial cell such as *Agrobacterium*. Further provided is a plant having stably incorporated into its genome a recombinant DNA construct that includes one or more EMEs described herein. Also provided is a seed that includes a recombinant DNA construct that includes one or more EMEs described herein.

In certain embodiments, the recombinant DNA construct that contains one or more EMEs described herein is operably linked to at least one heterologous nucleic acid sequence that includes a genetic sequence selected from the group consisting of: a reporter gene, a selection marker, a disease resistance gene, a herbicide resistance gene, an insect resistance gene; a gene involved in carbohydrate metabolism, a gene involved in fatty acid metabolism, a gene involved in amino acid metabolism, a gene involved in plant development, a gene involved in plant growth regulation, a gene involved in yield improvement, a gene involved in drought resistance, a gene involved in increasing nutrient utilization efficiency, a gene involved in cold resistance, a gene involved in heat resistance and a gene involved in salt resistance in plants. In certain embodiments, the recombinant DNA construct comprises at least one heterologous regulatory sequence that comprises a sequence that is substantially similar to an endogenous regulatory sequence of a maize gene. In certain embodiments, the recombinant DNA construct comprises at least one heterologous regulatory sequence that comprises a sequence that is substantially similar to an endogenous regulatory sequence of a soybean gene. In certain embodiments, the recombinant DNA construct comprises at least one heterologous regulatory sequence that comprises a sequence that is substantially similar to an endogenous regulatory sequence of a rice gene.

Also provided is a method of expressing a coding sequence or RNA in a plant the method includes expressing the recombinant DNA construct having one or more EMEs, wherein the at least one heterologous sequence comprises a coding sequence or encodes a functional RNA. A method of modulating the expression of a nucleotide sequence of interest in a plant, the method includes expressing a heterologous sequence that is operably linked to an expression modulating element sequence selected from the group consisting of SEQ ID NOS: 1-100, or a functional fragment thereof. In certain embodiments, the heterologous sequence confers an agronomic characteristic selected from the group consisting of: disease resistance, herbicide resistance, insect resistance, carbohydrate metabolism, fatty acid metabolism, amino acid metabolism, plant development, plant growth regulation, yield improvement, drought resistance, cold resistance, heat resistance, nutrient utilization efficiency, nitrogen use efficiency, and salt resistance.

Further provided is a method of modulating the expression of a nucleotide sequence of interest in a plant, the method includes expressing a polynucleotide sequence that is operably linked to a heterologous expression modulating element that is at least 95% identical to a sequence selected from the group consisting of SEQ ID NOS: 1-100, or a functional fragment thereof. In certain embodiments, the EME is in combination with an intron or a 5'UTR functional in a plant cell.

Provided is a plant stably transformed with a recombinant DNA construct comprising an EME selected from the group consisting of SEQ ID NOS: 1-100, or a functional fragment thereof, or a sequence that is at least 90% identical to one of SEQ ID NOS: 1-100, wherein the plant comprises the EME operably linked to a heterologous nucleic acid in the genome of the plant, wherein the EME modulates the expression of the heterologous nucleic acid.

Provided is a method of modifying the expression of an endogenous gene of a plant, the method comprising introducing an EME selected from the group consisting of SEQ ID NOS: 1-100, or a functional fragment thereof, or a sequence that is at least 90% identical to one of SEQ ID NOS: 1-100 such that the introduced EME is operably linked to modify the expression of the endogenous gene. In certain embodiments, the genome editing is performed through guided Cas9 endonuclease.

Provided is an isolated polynucleotide that includes a plant expression modulating element selected from the group consisting of SEQ ID NOS: 1-100, or a functional fragment thereof, wherein the expression modulating element is operably linked to a heterologous promoter sequence. In certain embodiments, the polynucleotide having the expression modulating element is operably linked to a heterologous coding sequence. In certain embodiments, the heterologous promoter sequence is present in the endogenous genomic sequence. In certain embodiments, the EME is present in multiple copies.

Provided is a method of generating a population of activation tagged plants comprising one or more copies of expression modulating element, the method comprising transforming a plurality of plants with a recombinant expression cassette comprising the one or more copies of the expression modulating element as an activation tag, wherein the expression modulating element is selected from the group consisting of SEQ ID NOS: 1-100, or a functional fragment thereof; and generating the population of plants that comprise the activation tag.

In another embodiment, this disclosure concerns a method of altering a marketable plant trait. The marketable plant trait concerns genes and proteins involved in disease resistance, herbicide resistance, insect resistance, carbohydrate metabolism, fatty acid metabolism, amino acid metabolism, plant development, plant growth regulation, yield improvement, drought resistance, cold resistance, heat resistance, and salt resistance.

In another embodiment, this disclosure concerns a recombinant DNA construct comprising a heterologous nucleotide sequence. The heterologous nucleotide sequence encodes a protein involved in disease resistance, herbicide resistance, insect resistance; carbohydrate metabolism, fatty acid metabolism, amino acid metabolism, plant development, plant growth regulation, yield improvement, drought resistance, cold resistance, heat resistance, or salt resistance in plants.

Further provided is a method of modulating expression of an endogenous polynucleotide in a plant cell, the method includes providing a deaminase polypeptide operably associated with a site-specific DNA binding polypeptide, whereby the deaminase polypeptide engineers one or more base changes such that at least one copy of a polynucleotide comprising the sequence selected from the group consisting of SEQ ID NOS: 1-100, or a functional fragment thereof, is created in a regulatory region of the endogenous polynucleotide, thereby modulating expression of the endogenous polynucleotide in the plant cell. In certain embodiments, the deaminase is an adenine deaminase or a guanine deaminase. In certain embodiments, the site-specific DNA binding polypeptide is an inactivated Cas endonuclease (e.g., dCas9). In certain embodiments, the inactivated Cas endonuclease is Cas9 or Cpf1, wherein the Cas9 or Cpf1 does not create a double-strand break but provides site-specific binding. In certain embodiments, the deaminase is fused to the Cas endonuclease. In certain embodiments, the regulatory region is the promoter region of the endogenous polynucleotide. In certain embodiments, the endogenous polynucleotide encodes a polypeptide or an RNA (e.g., microRNA (miRNA)) involved in pest protection, disease resistance, herbicide tolerance, drought tolerance, cold tolerance, increased oil and/or protein content, or an improved agronomic characteristic.

BRIEF DESCRIPTION OF THE DRAWINGS AND SEQUENCE LISTING

The disclosure can be more fully understood from the following detailed description and the accompanying drawing and Sequence Listing that form a part of this application, which are incorporated herein by reference.

FIG. 1 provides the experimental results of transient evaluation of EMEs in rice callus using the GUS reporter gene. The darkened staining is an indicator of GUS gene expression.

The sequence descriptions summarize the Sequence Listing attached hereto, which is hereby incorporated by reference. The Sequence Listing contains one letter codes for nucleotide sequence characters and the single and three letter codes for amino acids as defined in the IUPAC-IUB standards described in *Nucleic Acids Research* 13:3021-3030 (1985) and in the *Biochemical Journal* 219(2):345-373 (1984).

TABLE 1

Sequence Listing Description

| SEQ ID NO: | Size (bp) | EME Name |
|---|---|---|
| 1 | 30 | 1X-SF-Os-ENHs-4-1 |
| 2 | 30 | 1X-SF-At-ENH_9 |
| 3 | 31 | 1X-SF-At-ENH_23 |
| 4 | 31 | 1X-SF-At-ENH_25-1 |
| 5 | 31 | 1X-SF-At-ENH_25-2 |
| 6 | 31 | 1X-SF-At-ENH_25-3 |
| 7 | 31 | 1X-SF-Os-ENHs-1-1 |
| 8 | 31 | 1X-SF-Os-ENHs-1-2 |
| 9 | 31 | 1X-SF-At-ENH_1 |
| 10 | 31 | 1X-SF-Os-ENHs-4-2 |
| 11 | 31 | 1X-SF-Os-ENHs-28-1 |
| 12 | 44 | 1X-CP-MF-At-ENH-13-1 |
| 13 | 46 | 1X-CP-MF-At-ENH-21 |

TABLE 1-continued

Sequence Listing Description

| SEQ ID NO: | Size (bp) | EME Name |
|---|---|---|
| 14 | 51 | 1X-SF-Os-ENHs-12 |
| 15 | 30 | 1X-CP-Os-EME-1 |
| 16 | 30 | 1X-CP-Os-EME-2 |
| 17 | 30 | 1X-CP-Os-EME-3 |
| 18 | 30 | 1X-CP-Os-EME-4 |
| 19 | 30 | 1X-CP-Os-EME-5 |
| 20 | 30 | 1X-CP-Os-EME-6 |
| 21 | 30 | 1X-CP-Os-EME-7 |
| 22 | 30 | 1X-CP-Os-EME-8 |
| 23 | 30 | 1X-CP-Os-EME-9 |
| 24 | 30 | 1X-CP-Os-EME-10 |
| 25 | 30 | 1X-CP-Os-EME-11 |
| 26 | 30 | 1X-CP-Os-EME-12 |
| 27 | 30 | 1X-CP-Os-EME-13 |
| 28 | 30 | 1X-CP-Os-EME-14 |
| 29 | 30 | 1X-CP-Os-EME-15 |
| 30 | 30 | 1X-CP-Os-EME-16 |
| 31 | 30 | 1X-CP-Os-EME-17 |
| 32 | 30 | 1X-CP-Os-EME-18 |
| 33 | 30 | 1X-CP-Os-EME-19 |
| 34 | 30 | 1X-CP-Os-EME-20 |
| 35 | 30 | 1X-CP-Os-EME-21 |
| 36 | 30 | 1X-CP-Os-EME-22 |
| 37 | 30 | 1X-CP-Os-EME-23 |
| 38 | 30 | 1X-CP-Os-EME-24 |
| 39 | 30 | 1X-CP-Os-EME-25 |
| 40 | 30 | 1X-CP-Os-EME-26 |
| 41 | 30 | 1X-CP-Os-EME-27 |
| 42 | 30 | 1X-CP-Os-EME-28 |
| 43 | 30 | 1X-CP-Os-EME-29 |
| 44 | 30 | 1X-CP-Os-EME-30 |
| 45 | 30 | 1X-CP-Os-EME-31 |
| 46 | 30 | 1X-CP-Os-EME-32 |
| 47 | 30 | 1X-CP-Os-EME-33 |
| 48 | 30 | 1X-CP-Os-EME-34 |
| 49 | 30 | 1X-CP-Os-EME-35 |
| 50 | 30 | 1X-CP-Os-EME-36 |
| 51 | 30 | 1X-CP-Os-EME-37 |
| 52 | 30 | 1X-CP-Os-EME-38 |
| 53 | 30 | 1X-CP-Os-EME-39 |
| 54 | 30 | 1X-CP-Os-EME-40 |
| 55 | 30 | 1X-CP-Os-EME-41 |
| 56 | 30 | 1X-CP-Os-EME-42 |
| 57 | 30 | 1X-CP-Os-EME-43 |
| 58 | 30 | 1X-CP-Os-EME-44 |
| 59 | 30 | 1X-CP-Os-EME-45 |
| 60 | 30 | 1X-CP-Os-EME-46 |
| 61 | 30 | 1X-CP-Os-EME-47 |
| 62 | 30 | 1X-CP-Os-EME-48 |
| 63 | 30 | 1X-CP-Os-EME-49 |
| 64 | 30 | 1X-CP-Os-EME-50 |
| 65 | 30 | 1X-CP-Os-EME-51 |
| 66 | 30 | 1X-CP-Os-EME-52 |
| 67 | 30 | 1X-CP-Os-EME-53 |
| 68 | 30 | 1X-CP-Os-EME-54 |
| 69 | 30 | 1X-CP-Os-EME-55 |
| 70 | 30 | 1X-CP-Os-EME-56 |
| 71 | 30 | 1X-CP-Os-EME-57 |
| 72 | 30 | 1X-CP-Os-EME-58 |
| 73 | 30 | 1X-CP-Os-EME-59 |
| 74 | 30 | 1X-CP-Os-EME-60 |
| 75 | 30 | 1X-CP-Os-MCHR1 |
| 76 | 30 | 1X-CP-Os-MCHR2 |
| 77 | 30 | 1X-CP-Os-MCHR4 |
| 78 | 30 | 1X-CP-Os-MCHR12 |
| 79 | 31 | 1X-SF-Os-ENH-15-1 |
| 80 | 31 | 1X-SF-Os-ENH-15-2 |
| 81 | 31 | 1X-SF-Os-ENH-15-3 |
| 82 | 31 | 1X-SF-Os-ENH-17 |
| 83 | 21 | 1X-SF-Os-ENHs-4-1-1 |
| 84 | 11 | 1X-SF-Os-ENHs-4-1-2 |
| 85 | 21 | 1X-SF-Os-ENHs-4-1-3 |
| 86 | 11 | 1X-SF-Os-ENHs-4-1-4 |
| 87 | 10 | 1X-SF-Os-ENHs-4-1-5 |
| 88 | 10 | 1X-CP-Os-EME-1-1 |
| 89 | 10 | 1X-CP-Os-EME-4-1 |

TABLE 1-continued

Sequence Listing Description

| SEQ ID NO: | Size (bp) | EME Name |
|---|---|---|
| 90 | 10 | 1X-CP-Os-EME-15-1 |
| 91 | 10 | 1X-CP-Os-EME-29-1 |
| 92 | 10 | 1X-CP-Os-EME-32-1 |
| 93 | 10 | 1X-CP-Os-EME-39-1 |
| 94 | 10 | 1X-CP-Os-EME-49-1 |
| 95 | 10 | 1X-CP-Os-EME-52-1 |
| 96 | 10 | 1X-CP-Os-MCHR1-1 |
| 97 | 10 | 1X-CP-Os-MCHR2-1 |
| 98 | 10 | 1X-CP-Os-MCHR4-1 |
| 99 | 10 | 1X-CP-Os-MCHR5-1 |
| 100 | 10 | 1X-CP-Os-MCHR12-1 |

DETAILED DESCRIPTION

The disclosure of all patents, patent applications, and publications cited herein are incorporated by reference in their entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As used herein "isolated polynucleotide" generally refers to a polymer of ribonucleotides (RNA) or deoxyribonucleotides (DNA) that is single- or double-stranded, optionally containing synthetic, non-natural or altered nucleotide bases. An isolated polynucleotide in the form of DNA may be comprised of one or more segments of cDNA, genomic DNA or synthetic DNA.

The terms "polynucleotide", "polynucleotide sequence", "nucleic acid sequence", "nucleic acid fragment", and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

Provided herein are plants, plant cells, plant parts, seed, and grain comprising an introduced targeted genetic modification in a regulatory region of an endogenous polynucleotide so that the regulatory region of the polynucleotide comprises an expression modulating element "EME" comprising at least one copy of an EME sequence described herein. In certain embodiments, the EME comprises at least one copy of a polynucleotide sequence selected from the group consisting of SEQ ID NOS: 1-100 or functional fragments thereof. In certain embodiments, the EME comprises at least one copy of a polynucleotide that is at least 80% (e.g., 80, 81, 82, 83, 84, 85, 86, 87, 88, 89, 90, 91, 92, 93, 94, 95, 96, 97, 98, or 99) identical to any one of SEQ ID NOS: 1-100.

Also provided herein are methods of modulating expression of an endogenous polynucleotide in a plant cell, comprising introducing a targeted genetic modification in a regulatory region of the endogenous polynucleotide so that the regulatory region of the polynucleotide comprises at least one expression modulating element "EME" comprising an EME described herein. In certain embodiments, the method comprises (a) introducing in a regenerable plant cell a targeted genetic modification in a regulatory region of an endogenous polynucleotide so that the regulatory region comprises at least on EME sequence described herein; and (b) generating the plant, wherein the expression of the endogenous polynucleotide is increased compared to a control plant not comprising the EME. In certain embodiments, the EME comprises at least one copy of a polynucleotide sequence selected from the group consisting of SEQ ID NOS: 1-100 or functional fragments thereof. In certain embodiments, the EME comprises a polynucleotide sequence that is at least 80% to any one of SEQ ID NOS: 1-100.

"Expression modulating/modulation element" or "EME" as used herein refers to a nucleotide sequence that up- or down-regulates the expression of one or more plant genes. EMEs may have one or more copies of the same sequence arranged head-to-head, tail-to-head, or head-to-tail or a combination thereof configurations. EMEs are derived from plant sequences, or from bacterial or viral enhancer elements. In certain embodiments, the EME for use in the methods and compositions herein comprises a polynucleotide sequence comprising any one of SEQ ID NOs: 1-100, or a functional fragment thereof.

A "functional fragment" as used herein refers to a portion or subsequence of an EME sequence described herein in which, the ability to modulate (e.g., increase or decrease) gene expression is retained. Functional fragments can be obtained and tested via methods described herein, such as site-directed mutagenesis and synthetic construction. In certain embodiments, of the methods and compositions described herein, the functional fragment comprises at least 5 (e.g., at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27 at least 28, at least 29, at least 30) contiguous nucleotides of any one of SEQ ID NOs: 1-82. In certain embodiments, of the methods and compositions described herein, the functional fragment comprises the nucleotide sequence of any one of SEQ ID NOs: 83-100.

In certain embodiments, of the methods and compositions described herein the targeted genetic modification to introduce the EME alters one or more nucleotides in the regulatory region of the endogenous polynucleotide. In certain embodiments, the EME is introduced by altering no more than 20 (e.g., no more than 19, no more than 18, no more than 17, no more than 16, no more than 15, no more than 14, no more than 13, no more than 12, no more than 11, no more than 10, no more than 9, no more than 8, no more than 7, no more than 6, no more than 5, no more than 4, no more than 3, no more than 2) nucleotides in the regulatory region of the endogenous polynucleotide.

In certain embodiments, of the methods and compositions described herein, the EME further comprises additional copies of the expression modulating element such that about 2× to 30× copies of the EMEs are present in the regulatory region of the endogenous polynucleotide or a recombinant polynucleotide. In certain embodiments, when more than one copy of the EME is present, it can be present in one or more of the configurations selected from the group consisting of: head to head, head to tail, tail to head, tail to tail, and a combination thereof. In certain embodiments, the additional copies are separated by a spacer sequence, which may include about 1 to 50 nucleotides. In certain embodiments, the EME is a combination of one or more copies of heterologous expression elements. In certain embodiments, of the methods and compositions described herein, when one or more copies of the EMEs are present, the regulatory region is created by altering no more than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 27, 38, 39 or 40 nucleotides in the regulatory region of the endogenous polynucleotide.

"Genetic modification," "DNA modification," and the like refers to a site-specific modification that alters or changes the nucleotide sequence at a specific genomic locus of the plant. The genetic modification of the compositions and methods described herein may be any modification known in the art such as, for example, insertion, deletion, single nucleotide polymorphism (SNP), and or a polynucleotide modification.

As used herein, a "targeted" genetic modification or "targeted" DNA modification, refers to the direct manipulation of an organism's genes. The targeted modification may be introduced using any technique known in the art, such as, for example, plant breeding, genome editing, or single locus conversion. Additionally, the targeted DNA modification in the genomic locus may be located anywhere in the genomic locus, such as, for example, a coding region of the encoded polypeptide (e.g., exon), or a regulatory region.

Various methods can be used to introduce the targeted genetic modification into the regulatory region of an endogenous polynucleotide of the plant, plant part, plant cell, seed, and/or grain described herein. In certain embodiments, the targeted DNA modification is through a genome modification technique selected from the group consisting of a polynucleotide-guided endonuclease, CRISPR-Cas endonucleases, base editing deaminases, zinc finger nuclease, a transcription activator-like effector nuclease (TALEN), or engineered site-specific meganuclease or a site-specific base edit mediated by an C·G to T·A or an A·T to G·C base editing deaminase enzymes.

In certain embodiments, of the methods and compositions described herein, the genome modification may be facilitated through the induction of a double-stranded break (DSB) or single-strand break, in a defined position in the genome near the desired alteration. DSBs can be induced using any DSB-inducing agent available, including, but not limited to, TALENs, meganucleases, zinc finger nucleases, Cas9-gRNA systems (based on bacterial CRISPR-Cas systems), guided cpf1 endonuclease systems, and the like. In some embodiments, the introduction of a DSB can be combined with the introduction of a polynucleotide modification template.

In certain embodiments, of the methods and compositions described herein, the expression of the endogenous polynucleotide comprising the EME in a regulatory region is increased in a plant cell compared to a control plant cell not comprising the EME. In certain embodiments, of the methods and compositions described herein, the expression of the endogenous polynucleotide is decreased in a plant cell compared to a control plant cell not comprising the EME.

The term "expression", as used herein, generally refers to the production of a functional end-product e.g., an mRNA, a protein (precursor or mature), or a microRNA (precursor or mature).

"Altering expression" or "modulating expression" generally refers to the production of gene product(s) in plants in amounts or proportions that differ significantly from the amount of the gene product(s) produced by the corresponding wild-type plants (i.e., expression is increased or decreased). "Increased expression" or the like, as used herein, refers to any detectable elevation in expression of the end-product as compared to a control (e.g., a polynucleotide that is not operably linked to an EME). "Decreased expression" or the like, as used herein, refers to any detectable reduction in expression of the end-product as compared to a control (e.g., a polynucleotide that is not operably linked to an EME). A person of ordinary skill in the art can readily determine changes in expression level (e.g., changes in mRNA, protein, or microRNA expression) using routine methods in the art such as PCR and Western blotting.

In certain embodiments, of the methods and compositions described herein the expression modulating element is heterologous to the polynucleotide. In certain embodiments, the expression modulating element is heterologous to a promoter functional in the plant. In certain embodiments, the expression modulating element is heterologous to both the polynucleotide and to the promoter functional in the plant.

A "heterologous nucleotide sequence" generally refers to a sequence that is not naturally occurring with the EME of the disclosure. While this nucleotide sequence is heterologous to the EME sequence, it may be homologous, or native, or heterologous, or foreign, to the plant host. However, it is recognized that the instant EMEs may be used with their native coding sequences to increase or decrease expression resulting in a change in phenotype in the transformed seed. The terms "heterologous nucleotide sequence", "heterologous sequence", "heterologous nucleic acid fragment", and "heterologous nucleic acid sequence" are used interchangeably herein.

In certain embodiments, of the methods and compositions described herein, the EME is inserted upstream of the transcriptional start site of the endogenous polynucleotide. In certain embodiments, the EME is inserted downstream of the transcriptional start site of the endogenous polynucleotide. In certain embodiments, the EME is inserted within about 10 to about 5000 bp from the transcriptional start site of the endogenous polynucleotide. This location range also includes about 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 1000, 2000, 3000, 4000 and 5000 nucleotides from the TSS.

In certain embodiments, of the methods and compositions described herein, the EME is inserted into the regulatory region (e.g., promoter) of the endogenous polynucleotide such that the expression modulating element is operably linked to the endogenous polynucleotide. In certain embodiments, the EME is inserted upstream of the endogenous promoter. In certain embodiments, the EME is inserted in the endogenous promoter region. In certain embodiments, the EME is inserted within 100 base pairs (bp) (e.g., within 90 bp, within 80 within 70 bp, within 60 bp, within 50 bp, within 40 bp, within 30 bp, within 20 bp, or within 10 bp) of the TATA box of the endogenous promoter.

The term "operably linked" or "functionally linked" generally refers to the association of nucleic acid sequences on a single nucleic acid fragment so that the function of one is affected by the other. For example, an EME is operably linked with a coding sequence (e.g., endogenous polynucleotide) when it is capable of modulating the expression (e.g., increasing or decreasing) of that coding sequence. Coding sequences can be operably linked to regulatory sequences in sense or antisense orientation.

A "regulatory region" generally refers to a non-coding region of a gene that comprises regulatory sequences (e.g., regulatory elements) involved in regulating the transcription of the gene. Regulatory regions may be present upstream of the coding sequence of the gene of interest and/or downstream of the coding sequence of the gene of interest. A person of ordinary skill in the art can identify regulatory sequences of a gene of interest (e.g., regulatory elements of an endogenous polynucleotide) using methods known in the art.

A regulatory element generally refers to a transcriptional regulatory element involved in regulating the transcription of a nucleic acid molecule such as a gene or a target gene. The regulatory element is a nucleic acid and may include a promoter, an enhancer, an intron, a 5'-untranslated region (5'-UTR, also known as a leader sequence), or a 3'-UTR or a combination thereof. A regulatory element may act in "cis" or "trans", and generally it acts in "cis", i.e. it activates expression of genes located on the same nucleic acid molecule, e.g. a chromosome, where the regulatory element is located. The nucleic acid molecule regulated by a regulatory element does not necessarily have to encode a functional peptide or polypeptide, e.g., the regulatory element can modulate the expression of a short interfering RNA or an anti-sense RNA.

An enhancer element is any nucleic acid molecule that increases transcription of a nucleic acid molecule when functionally linked to a promoter regardless of its relative position. An enhancer may be an innate element of the promoter or a heterologous element inserted to enhance the level or tissue-specificity of a promoter.

A repressor (also sometimes called herein silencer) is defined as any nucleic acid molecule which inhibits the transcription when functionally linked to a promoter regardless of relative position.

An "intron" is an intervening sequence in a gene that is transcribed into RNA but is then excised in the process of generating the mature mRNA. The term is also used for the excised RNA sequences. An "exon" is a portion of the sequence of a gene that is transcribed and is found in the mature messenger RNA derived from the gene but is not necessarily a part of the sequence that encodes the final gene product. In certain embodiments, of the compositions and methods described herein, the EME is operably linked to a heterologous intron. In certain embodiments, of the compositions and methods described herein, the EME is inserted into the genome in combination with a heterologous intron.

The 5' untranslated region (5'UTR) (also known as a translational leader sequence or leader RNA) is the region of an mRNA that is directly upstream from the initiation codon. This region is involved in the regulation of translation of a transcript by differing mechanisms in viruses, prokaryotes and eukaryotes. In certain embodiments, of the compositions and methods described herein, the EME is operably linked to a heterologous 5'UTR. In certain embodiments, of the compositions and methods described herein, the EME is inserted into the genome in combination with a heterologous 5'UTR.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"RNA transcript" generally refers to a product resulting from RNA polymerase-catalyzed transcription of a DNA sequence. When an RNA transcript is a perfect complimentary copy of a DNA sequence, it is referred to as a primary transcript or it may be a RNA sequence derived from posttranscriptional processing of a primary transcript and is referred to as a mature RNA. "Messenger RNA" ("mRNA") generally refers to RNA that is without introns and that can be translated into protein by the cell. "cDNA" generally refers to a DNA that is complementary to and synthesized from an mRNA template using the enzyme reverse transcriptase. The cDNA can be single-stranded or converted into the double-stranded by using the Klenow fragment of DNA polymerase I. "Sense" RNA generally refers to RNA transcript that includes mRNA and so can be translated into protein within a cell or in vitro. "Antisense RNA" generally refers to a RNA transcript that is complementary to all or part of a target primary transcript or mRNA and that blocks expression or transcripts accumulation of a target gene. The complementarity of an antisense RNA may be with any part of the specific gene transcript, i.e. at the 5' non-coding sequence, 3' non-coding sequence, introns, or the coding sequence. "Functional RNA" generally refers to antisense RNA, ribozyme RNA, or other RNA that may not be translated but yet has an effect on cellular processes.

A "promoter" generally refers to a nucleic acid fragment capable of controlling transcription of another nucleic acid fragment. A promoter generally includes a core promoter (also known as minimal promoter) sequence that includes a minimal regulatory region to initiate transcription, that is a transcription start site. Generally, a core promoter includes a TATA box and a GC rich region associated with a CAAT box or a CCAAT box. These elements act to bind RNA polymerase II to the promoter and assist the polymerase in locating the RNA initiation site. Some promoters may not have a TATA box or CAAT box or a CCAAT box, but instead may contain an initiator element for the transcription initiation site. A core promoter is a minimal sequence required to direct transcription initiation and generally may not include enhancers or other UTRs. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Core promoters are often modified to produce artificial, chimeric, or hybrid promoters, and can further be used in combination with other regulatory elements, such as cis-elements, 5'UTRs, enhancers, or introns, that are either heterologous to an active core promoter or combined with its own partial or complete regulatory elements.

The term "cis-element" generally refers to transcriptional regulatory element that affects or modulates expression of an operably linked transcribable polynucleotide, where the transcribable polynucleotide is present in the same DNA sequence. A cis-element may function to bind transcription factors, which are trans-acting polypeptides that regulate transcription.

"Promoter functional in a plant" is a promoter capable of initiating transcription in plant cells whether or not its origin is from a plant cell.

"Tissue-specific promoter" and "tissue-preferred promoter" are used interchangeably to refer to a promoter that is expressed predominantly but not necessarily exclusively in one tissue or organ, but that may also be expressed in one specific cell.

"Developmentally regulated promoter" generally refers to a promoter whose activity is determined by developmental events.

"Constitutive promoter" generally refers to promoters active in all or most tissues or cell types of a plant at all or most developing stages. As with other promoters classified as "constitutive" (e.g. ubiquitin), some variation in absolute levels of expression can exist among different tissues or stages. The term "constitutive promoter" or "tissue-independent" are used interchangeably herein.

A "variant promoter" as used herein, is the sequence of the promoter or the sequence of a fragment of a promoter containing changes in which one or more nucleotides of the original sequence is deleted, added, and/or substituted, while substantially maintaining promoter function. One or more base pairs can be inserted, deleted, or substituted internally to a promoter. In the case of a promoter fragment, variant promoters can include changes affecting the transcription of a minimal promoter to which it is operably linked. Variant promoters can be produced, for example, by standard DNA mutagenesis techniques or by chemically synthesizing the variant promoter or a portion thereof.

Methods for construction of chimeric and variant promoters of the present disclosure include, but are not limited to, combining promoter elements of different promoters or duplicating portions or regions of one or more promoters. Those of skill in the art are familiar with the standard resource materials that describe specific conditions and procedures for the construction, manipulation, and isolation of macromolecules (e.g., polynucleotide molecules and plasmids), as well as the generation of recombinant organisms and the screening and isolation of polynucleotide molecules.

In some aspects of the present disclosure, the promoter fragments can comprise at least about 20 contiguous nucleotides, or at least about 50 contiguous nucleotides, or at least about 75 contiguous nucleotides, or at least about 100 contiguous nucleotides, or at least about 150 contiguous nucleotides, or at least about 200 contiguous nucleotides. In another aspect of the present disclosure, the promoter fragments can comprise at least about 250 contiguous nucleotides, or at least about 300 contiguous nucleotides, or at least about 350 contiguous nucleotides, or at least about 400 contiguous nucleotides, or at least about 450 contiguous nucleotides, or at least about 500 contiguous nucleotides, or at least about 550 contiguous nucleotides, or at least about 600 contiguous nucleotides, or at least about 650 contiguous nucleotides, or at least about 700 contiguous nucleotides, or at least about 750 contiguous nucleotides, or at least about 800 contiguous nucleotides, or at least about 850 contiguous nucleotides, or at least about 900 contiguous nucleotides, or at least about 950 contiguous nucleotides, or at least about 1000 contiguous nucleotides, or at least about 1050 contiguous nucleotides, or at least about 1200, 1300, 1400, 1500, 2000, 3000, 4000, 5000 contiguous nucleotides of a full length promoter and further may include an EME comprising any one of SEQ ID NOS: 1-100 or a functional fragment thereof. The nucleotides of such promoter fragments generally comprise the TATA recognition sequence of the particular promoter sequence. Such fragments may be obtained by use of restriction enzymes to cleave the naturally occurring promoter nucleotide sequences disclosed herein, by synthesizing a nucleotide sequence from the naturally occurring promoter DNA sequence or may be obtained through the use of PCR technology. In certain embodiments, of the compositions and methods described herein, the EME is operably linked to a minimal core promoter.

The polynucleotide sequence of the EMEs of the present disclosure (e.g., SEQ ID NOS: 1-100 or functional fragments thereof), may also be modified or altered to enhance their modulation characteristics or to produce substantially similar EME sequences. Sequences can be modified, for example by insertion, deletion, or replacement of template sequences through any modification approach. In certain embodiments, of the methods and compositions described herein modified EMEs of the present disclosure comprise a nucleotide sequence that is at least 80% (e.g., 80, 81, 82, 83, 84, 85, 86, 87, 88, 89, 90, 91, 92, 93, 94, 95, 96, 97, 98, or 99) identical to any one of SEQ ID NOS: 1-100.

Sequence alignments and percent identity calculations may be determined using a variety of comparison methods designed to detect similar or identical sequences including, but not limited to, the Megalign® program of the LASERGENE® bioinformatics computing suite (DNASTAR® Inc., Madison, WI). Unless stated otherwise, multiple alignment of the sequences provided herein were performed using the Clustal V method of alignment (Higgins and Sharp (1989) CABIOS. 5:151-153) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner. In certain embodiments, the % sequence identity is determined over the entire length of the molecule (nucleotide or amino acid).

The terms "substantially similar" and "corresponding substantially" as used herein refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant disclosure such as deletion or insertion of one or more nucleotides that do not substantially alter the functional properties of the resulting nucleic acid fragment relative to the initial, unmodified fragment. It is therefore understood, as those skilled in the art will appreciate, that the disclosure encompasses more than the specific exemplary sequences.

A "substantially similar sequence" generally refers to variants of the disclosed sequences such as those that result from site-directed mutagenesis, as well as synthetically derived sequences.

The present disclosure also provides a recombinant DNA construct comprising a polynucleotide sequence comprising at least one of the EME sequences described herein operably linked to a heterologous nucleic acid sequence. In certain embodiments, the EME comprises at least one copy of a polynucleotide sequence selected from the group consisting of SEQ ID NOS: 1-100 or functional fragments thereof. In certain embodiments, the EME comprises a polynucleotide sequence that is at least 80% to any one of SEQ ID NOS: 1-100.

The term "recombinant DNA construct" or "recombinant expression construct" is used interchangeably and generally refers to a discrete polynucleotide into which a nucleic acid sequence or fragment can be moved. Preferably, it is a plasmid vector or a fragment thereof comprising the promoters of the present disclosure. The choice of plasmid vector is dependent upon the method that will be used to transform host plants. The skilled artisan is well aware of the genetic elements that must be present on the plasmid vector in order to successfully transform, select and propagate host cells containing the heterologous nucleic acid sequence. The skilled artisan will also recognize that different independent transformation events will result in different levels and patterns of expression (Jones et al., EMBO J. 4:2411-2418 (1985); De Almeida et al., Mol. Gen. Genetics 218:78-86 (1989)), and thus that multiple events must be screened in order to obtain lines displaying the desired expression level and pattern. Such screening may be accomplished by PCR and Southern analysis of DNA, RT-PCR and Northern analysis of mRNA expression, Western analysis of protein expression, or phenotypic analysis.

The location of the EME in the recombinant DNA construct is not particularly limited so long as expression of the heterologous nucleic acid sequence in a cell is increased when the EME is present as compared to a control construct not comprising the EME. In certain embodiments, the recombinant DNA construct comprises at least one sequence that is substantially similar to an endogenous regulatory sequence of a maize gene. In certain embodiments, the EME is inserted upstream of the at least one regulatory sequence of the recombinant DNA construct. In certain embodiments, the EME is inserted downstream of the at least one regulatory sequence of the recombinant DNA construct. In certain embodiments, the EME is inserted in the at least one regulatory sequence of the recombinant DNA construct. In certain embodiments, the regulatory sequence for use in the recombinant DNA construct is heterologous to the to the heterologous nucleic acid sequence. In certain embodiments, the regulatory sequence for use in the recombinant DNA construct is a regulatory sequence of the heterologous nucleic acid sequence. In certain embodiments, the at least one regulatory sequence comprises a promoter functional in a plant. In certain embodiments, the EME is inserted in the promoter region. In certain embodiments, the EME is inserted within 100 base pairs (bp) (e.g., within 90 bp, within 80 within 70 bp, within 60 bp, within 50 bp, within 40 bp, within 30 bp, within 20 bp, or within 10 bp) of the TATA box of the promoter. In certain embodiments, the EME is inserted in combination with another regulatory sequence. In certain embodiments, the EME is inserted into the recombinant DNA construct in combination with an intron and/or a 5'UTR. In certain embodiments, when the EME is inserted in combination with another regulatory sequence, such as an intron and/or a 5'UTR, the EME can be sequence may be contiguous with the additional regulatory sequence or may be separated by a spacer. In certain embodiments, the spacer comprises between 1 to 200 base pairs.

Also provided herein are plants, plant cells, plant parts, seed, and grain comprising any of the recombinant DNA constructs described herein. In certain embodiments, the plant, plant cell, plant part, seed, or grain is transiently transformed with the recombinant DNA construct. In certain embodiments, the plant, plant cell, plant part, seed, or grain is stably transformed with the recombinant DNA construct.

"Transformation" as used herein generally refers to both stable transformation and transient transformation.

"Stable transformation" generally refers to the introduction of a nucleic acid fragment into a genome of a host organism resulting in genetically stable inheritance. Once stably transformed, the nucleic acid fragment is stably integrated in the genome of the host organism and any subsequent generation. Host organisms containing the transformed nucleic acid fragments are referred to as "transgenic" organisms.

"Transient transformation" generally refers to the introduction of a nucleic acid fragment into the nucleus, or DNA-containing organelle, of a host organism resulting in gene expression without genetically stable inheritance.

The present disclosure also provides a method of altering (increasing or decreasing) the expression of at least one heterologous nucleic acid fragment in a plant cell which comprises:

(a) introducing into a plant cell a recombinant expression construct described herein; and
(b) selecting plants containing a transformed plant cell wherein the expression of the heterologous nucleic acid fragment is increased or decreased as compared to a control plant or plant cell.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

In certain embodiments, the endogenous polynucleotide or heterologous nucleic acid of the recombinant DNA construct of the compositions and methods described herein encodes a polypeptide. The polypeptide encoded is not particularly limited and may be any gene of interest for which modulation (e.g., increase) of expression is desired. For example, modulation of expression may be desired to alter the phenotype of the plant, plant cell, plant part, seed, or grain.

Various changes in phenotype are of interest including, but not limited to, modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic characteristics and traits such as yield and heterosis increase, the choice of genes for transformation may change accordingly. General categories of genes of interest include, but are not limited to, those genes involved in information, such as zinc fingers, those involved in communication, such as kinases, and those involved in housekeeping, such as heat shock proteins. More specific categories, for example, include, but are not limited to, genes encoding important traits for agronomics, insect resistance, disease resistance, herbicide resistance, sterility, grain or seed characteristics, and commercial products. Genes of interest include, generally, those involved in oil, starch, carbohydrate, or nutrient metabolism as well as those affecting seed size, plant development, plant growth regulation, and yield improvement. Plant development and growth regulation also refer to the development and growth regulation of various parts of a plant, such as the flower, seed, root, leaf and shoot.

Other commercially desirable traits are genes and proteins conferring cold, heat, salt, and drought resistance.

Disease and/or insect resistance genes may encode resistance to pests that have great yield drag such as for example, Northern Corn Leaf Blight, head smut, anthracnose, soybean mosaic virus, soybean cyst nematode, root-knot nematode, brown leaf spot, Downy mildew, purple seed stain, seed decay and seedling diseases caused commonly by the fungi—*Pythium* sp., *Phytophthora* sp., *Rhizoctonia* sp., *Diaporthe* sp. Bacterial blight caused by the bacterium *Pseudomonas syringae* pv. Glycinea. Genes conferring insect resistance include, for example, *Bacillus thuringiensis* toxic protein genes (U.S. Pat. Nos. 5,366,892; 5,747,450; 5,737,514; 5,723,756; 5,593,881; and Geiser et al (1986) Gene 48:109); lectins (Van Damme et al. (1994) Plant Mol. Biol. 24:825); and the like.

Herbicide resistance traits may include genes coding for resistance to herbicides that act to inhibit the action of acetolactate synthase (ALS), in particular the sulfonylurea-type herbicides (e.g., the acetolactate synthase ALS gene containing mutations leading to such resistance, in particular the S4 and/or HRA mutations). The ALS-gene mutants encode resistance to the herbicide chlorsulfuron. Glyphosate acetyl transferase (GAT) is an N-acetyltransferase from *Bacillus licheniformis* that was optimized by gene shuffling for acetylation of the broad spectrum herbicide, glyphosate, forming the basis of a novel mechanism of glyphosate tolerance in transgenic plants (Castle et al. (2004) Science 304, 1151-1154).

Genes involved in plant growth and development have been identified in plants. One such gene, which is involved in cytokinin biosynthesis, is isopentenyl transferase (IPT). Cytokinin plays a critical role in plant growth and development by stimulating cell division and cell differentiation (Sun et al. (2003), Plant Physiol. 131: 167-176).

Also contemplated are heterologous nucleic acids encoding reporter genes or selection markers.

In certain embodiments, of the compositions and methods described herein, the endogenous polynucleotide or heterologous nucleic acid encodes a polypeptide that is involved in drought tolerance, disease resistance, herbicide tolerance, pest resistance, yield increase, yield stability, nitrogen utilization efficiency or a combination thereof.

In certain embodiments, of the compositions and methods described herein, the endogenous polynucleotide or heterologous nucleic acid is a microRNA or a microRNA precursor.

As used herein, the term "plant" includes plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the disclosure, provided that these parts comprise the introduced polynucleotides or genetic modification(s).

Examples of plant species for use in the compositions and methods described herein include, but are not limited to, maize (*Zea mays*), *Brassica* sp. (e.g., *B. napus*, *B. rapa*, *B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatas*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, conifers, turf grasses (including cool seasonal grasses and warm seasonal grasses).

Vegetables include, for example, tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing that which is disclosed include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow cedar (*Chamaecyparis nootkatensis*), and Poplar and Eucalyptus. In specific embodiments, plants of the present disclosure are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include, for example, grain plants that provide seeds of interest, oil-seed plants, and leguminous plants. Seeds of interest include, for example, grain seeds, such as corn, wheat, barley, rice, sorghum, rye, etc. Oil-seed plants include, for example, cotton, soybean, safflower, sunflower, Brassica, maize, alfalfa, palm, coconut, etc. Leguminous plants include beans and peas. Beans include guar, locust bean, fenugreek, soybean, garden beans, cowpea, mungbean, lima bean, fava bean, lentils, chickpea.

In certain embodiments, directed to methods utilizing EMEs and compositions containing EMEs the plant or plant cell is selected from the group comprising maize, rice, soybean, sunflower, wheat, canola, cotton, or sorghum.

The plant cells for use in the compositions and methods described herein may be a cell from any of the plants described herein.

For example, in certain embodiments, maize plants are provided that comprise, in their genome, a recombinant DNA construct comprising an EME comprising a polynucleotide sequence comprising at least one copy of a polynucleotide sequence selected from the group consisting of SEQ ID NOS: 1-100 or a functional fragment thereof. In other embodiments, maize plants are provided that comprise a targeted genetic modification in a regulatory region of an endogenous polynucleotide so that the regulatory region of the polynucleotide comprises an EME comprising at least one copy of an EME comprising a polynucleotide sequence selected from the group consisting of SEQ ID NOS: 1-100 or functional fragments thereof.

In addition to modulating gene expression, the expression modulating elements disclosed herein are also useful as probes or primers in nucleic acid hybridization experiments. The nucleic acid probes and primers of the EMEs hybridize under stringent conditions to a target DNA sequence. A "probe" is generally referred to an isolated/synthesized nucleic acid to which, is attached a conventional detectable label or reporter molecule, such as for example, a radioactive isotope, ligand, chemiluminescent agent, bioluminescent molecule, fluorescent label or dye, or enzyme. Such detectable labels may be covalently linked or otherwise physically associated with the probe. "Primers" generally referred to isolated/synthesized nucleic acids that hybridize to a complementary target DNA strand which is then extended along the target DNA strand by a polymerase, e.g., a DNA polymerase. Primer pairs often used for amplification of a target nucleic acid sequence, e.g., by the polymerase chain reaction (PCR) or other conventional nucleic-acid amplification methods. Primers are also used for a variety of sequencing reactions, sequence captures, and other sequence-based amplification methodologies. Primers are generally about 15, 20, 25 nucleotides or more, and probes can also be longer about 30, 40, 50 and up to a few hundred base pairs. Such probes and primers are used in hybridization reactions to target DNA or RNA sequences under high stringency hybridization conditions or under lower stringency conditions, depending on the need.

Moreover, the skilled artisan recognizes that substantially similar nucleic acid sequences encompassed by this disclosure are also defined by their ability to hybridize, under moderately stringent conditions (for example, 0.5×SSC, 0.1% SDS, 60° C.) with the sequences exemplified herein, or to any portion of the nucleotide sequences reported herein and which are functionally equivalent to the promoter of the disclosure. Estimates of such homology are provided by either DNA-DNA or DNA-RNA hybridization under conditions of stringency as is well understood by those skilled in the art (Hames and Higgins, Eds.; In Nucleic Acid Hybridisation; IRL Press: Oxford, U.K., 1985). Stringency conditions can be adjusted to screen for moderately similar fragments, such as homologous sequences from distantly related organisms, to highly similar fragments, such as genes that duplicate functional enzymes from closely related organisms. Post-hybridization washes partially determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. Another set of stringent conditions uses higher temperatures in which the washes are identical to those above except for the temperature of the final two 30 min washes in 0.2×SSC, 0.5% SDS was increased to 60° C. Another set of highly stringent conditions uses two final washes in 0.1×SSC, 0.1% SDS at 65° C.

I. Gene Editing

In some embodiments, gene editing may be facilitated through the induction of a double-stranded break (DSB) in a defined position in the genome near the desired alteration. DSBs can be induced using any DSB-inducing agent available, including, but not limited to, TALENs, meganucleases, zinc finger nucleases, Cas9-gRNA systems (based on bacterial CRISPR-Cas systems), and the like. In some embodiments, the introduction of a DSB can be combined with the introduction of a polynucleotide modification template.

A polynucleotide modification template can be introduced into a cell by any method known in the art, such as, but not limited to, transient introduction methods, transfection, electroporation, microinjection, particle mediated delivery, topical application, whiskers mediated delivery, delivery via cell-penetrating peptides, or mesoporous silica nanoparticle (MSN)-mediated direct delivery.

The polynucleotide modification template can be introduced into a cell as a single stranded polynucleotide molecule, a double stranded polynucleotide molecule, or as part of a circular DNA (vector DNA). The polynucleotide modification template can also be tethered to the guide RNA and/or the Cas endonuclease. Tethered DNAs can allow for co-localizing target and template DNA, useful in genome editing and targeted genome regulation, and can also be useful in targeting post-mitotic cells where function of endogenous HR machinery is expected to be highly diminished (Mali et al. 2013 *Nature Methods* Vol. 10: 957-963.) The polynucleotide modification template may be present transiently in the cell or it can be introduced via a viral replicon.

A "modified nucleotide" or "edited nucleotide" refers to a nucleotide sequence of interest that comprises at least one alteration when compared to its non-modified nucleotide sequence. Such "alterations" include, for example: (i) replacement of at least one nucleotide, (ii) a deletion of at least one nucleotide, (iii) an insertion of at least one nucleotide, or (iv) any combination of (i)-(iii).

The term "polynucleotide modification template" includes a polynucleotide that comprises at least one nucleotide modification when compared to the nucleotide sequence to be edited. A nucleotide modification can be at least one nucleotide substitution, addition or deletion. Optionally, the polynucleotide modification template can further comprise homologous nucleotide sequences flanking the at least one nucleotide modification, wherein the flanking homologous nucleotide sequences provide sufficient homology to the desired nucleotide sequence to be edited.

The process for editing a genomic sequence combining DSB and modification templates generally comprises: providing to a host cell, a DSB-inducing agent, or a nucleic acid encoding a DSB-inducing agent, that recognizes a target sequence in the chromosomal sequence and is able to induce a DSB in the genomic sequence, and at least one polynucleotide modification template comprising at least one nucleotide alteration when compared to the nucleotide sequence to be edited. The polynucleotide modification template can further comprise nucleotide sequences flanking the at least one nucleotide alteration, in which the flanking sequences are substantially homologous to the chromosomal region flanking the DSB.

The endonuclease can be provided to a cell by any method known in the art, for example, but not limited to transient introduction methods, transfection, microinjection, and/or topical application or indirectly via recombination constructs. The endonuclease can be provided as a protein or as a guided polynucleotide complex directly to a cell or indirectly via recombination constructs. The endonuclease can be introduced into a cell transiently or can be incorporated into the genome of the host cell using any method known in the art. In the case of a CRISPR-Cas system, uptake of the endonuclease and/or the guided polynucleotide into the cell can be facilitated with a Cell Penetrating Peptide (CPP) as described in WO2016073433 published May 12, 2016.

As used herein, a "genomic region" is a segment of a chromosome in the genome of a cell that is present on either side of the target site or, alternatively, also comprises a portion of the target site. The genomic region can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800. 5-2900, 5-3000, 5-3100 or more bases such that the genomic region has sufficient homology to undergo homologous recombination with the corresponding region of homology.

TAL effector nucleases (TALEN) are a class of sequence-specific nucleases that can be used to make double-strand breaks at specific target sequences in the genome of a plant or other organism. (Miller et al. (2011) *Nature Biotechnology* 29:143-148).

Endonucleases are enzymes that cleave the phosphodiester bond within a polynucleotide chain. Endonucleases include restriction endonucleases, which cleave DNA at specific sites without damaging the bases, and meganucleases, also known as homing endonucleases (HEases), which like restriction endonucleases, bind and cut at a specific recognition site, however the recognition sites for meganucleases are typically longer, about 18 bp or more (patent application PCT/US12/30061, filed on Mar. 22, 2012). Meganucleases have been classified into four families based on conserved sequence motifs, the families are the LAGLIDADG, GIY-YIG, H—N—H, and His-Cys box families. These motifs participate in the coordination of metal ions and hydrolysis of phosphodiester bonds. HEases are notable for their long recognition sites, and for tolerating some sequence polymorphisms in their DNA substrates. The naming convention for meganuclease is similar to the convention for other restriction endonuclease. Meganucleases are also characterized by prefix F-, I-, or PI- for enzymes encoded by free-standing ORFs, introns, and inteins, respectively. One step in the recombination process involves polynucleotide cleavage at or near the recognition site. The cleaving activity can be used to produce a double-strand break. For reviews of site-specific recombinases and their recognition sites, see, Sauer (1994) *Curr Op Biotechnol* 5:521-7; and Sadowski (1993) *FASEB* 7:760-7. In some examples the recombinase is from the Integrase or Resolvase families.

Zinc finger nucleases (ZFNs) are engineered double-strand break inducing agents comprised of a zinc finger DNA binding domain and a double-strand-break-inducing agent domain. Recognition site specificity is conferred by the zinc finger domain, which typically comprising two, three, or four zinc fingers, for example having a C2H2 structure, however other zinc finger structures are known and have been engineered. Zinc finger domains are amenable for designing polypeptides which specifically bind a selected polynucleotide recognition sequence. ZFNs include an engineered DNA-binding zinc finger domain linked to a non-specific endonuclease domain, for example nuclease domain from a Type IIs endonuclease such as FokI. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, a 3 finger domain recognized a sequence of 9 contiguous nucleotides, with a dimerization requirement of the nuclease, two sets of zinc finger triplets are used to bind an 18 nucleotide recognition sequence.

Genome editing using DSB-inducing agents, such as Cas9-gRNA complexes, has been described, for example in U.S. Patent Application US 2015-0082478 A1, published on Mar. 19, 2015, WO2015/026886 A1, published on Feb. 26, 2015, WO2016007347, published on Jan. 14, 2016, and WO201625131, published on Feb. 18, 2016, all of which are incorporated by reference herein.

The term "Cas gene" herein refers to a gene that is generally coupled, associated or close to, or in the vicinity of flanking CRISPR loci in bacterial systems. The terms "Cas gene", "CRISPR-associated (Cas) gene" are used interchangeably herein. The term "Cas endonuclease" herein refers to a protein encoded by a Cas gene. A Cas endonuclease herein, when in complex with a suitable polynucleotide component, is capable of recognizing, binding to, and optionally nicking or cleaving all or part of a specific DNA target sequence. A Cas endonuclease described herein comprises one or more nuclease domains. Cas endonucleases of the disclosure includes those having a HNH or HNH-like nuclease domain and/or a RuvC or RuvC-like nuclease domain. A Cas endonuclease of the disclosure includes a Cas9 protein, a Cpf1 protein, a C2c1 protein, a C2c2 protein, a C2c3 protein, Cas3, Cas 5, Cas7, Cas8, Cas10, or complexes of these.

In addition to the double-strand break inducing agents, site-specific base conversions can also be achieved to engineer one or more nucleotide changes to create one or more EMEs described herein into the genome. These include for example, a site-specific base edit mediated by an C·G to T·A or an A·T to G·C base editing deaminase enzymes (Gaudelli et al., Programmable base editing of A·T to G·C in genomic DNA without DNA cleavage." Nature (2017); Nishida et al. "Targeted nucleotide editing using hybrid prokaryotic and vertebrate adaptive immune systems." Science 353 (6305) (2016); Komor et al. "Programmable editing of a target base in genomic DNA without double-stranded DNA cleavage." Nature 533 (7603) (2016):420-4. Catalytically dead dCas9 fused to a cytidine deaminase or an adenine deaminase protein becomes a specific base editor that can alter DNA bases without inducing a DNA break. Base editors convert C->T (or G->A on the opposite strand) or an adenine base editor that would convert adenine to inosine, resulting in an A->G change within an editing window specified by the gRNA.

As used herein, the terms "guide polynucleotide/Cas endonuclease complex", "guide polynucleotide/Cas endonuclease system", "guide polynucleotide/Cas complex", "guide polynucleotide/Cas system", "guided Cas system" are used interchangeably herein and refer to at least one guide polynucleotide and at least one Cas endonuclease that are capable of forming a complex, wherein said guide polynucleotide/Cas endonuclease complex can direct the Cas endonuclease to a DNA target site, enabling the Cas endonuclease to recognize, bind to, and optionally nick or cleave (introduce a single or double strand break) the DNA target site. A guide polynucleotide/Cas endonuclease complex herein can comprise Cas protein(s) and suitable polynucleotide component(s) of any of the four known CRISPR systems (Horvath and Barrangou, 2010, Science 327:167-170) such as a type I, II, or III CRISPR system. A Cas endonuclease unwinds the DNA duplex at the target sequence and optionally cleaves at least one DNA strand, as mediated by recognition of the target sequence by a polynucleotide (such as, but not limited to, a crRNA or guide RNA) that is in complex with the Cas protein. Such recognition and cutting of a target sequence by a Cas endonuclease typically occurs if the correct protospacer-adjacent motif (PAM) is located at or adjacent to the 3' end of the DNA target sequence. Alternatively, a Cas protein herein may lack DNA cleavage or nicking activity, but can still specifically bind to a DNA target sequence when complexed with a suitable RNA component. (See also U.S. Patent Application US 2015-0082478 A1, published on Mar. 19, 2015 and US 2015-0059010 A1, published on Feb. 26, 2015, both are hereby incorporated in its entirety by reference).

A guide polynucleotide/Cas endonuclease complex can cleave one or both strands of a DNA target sequence. A guide polynucleotide/Cas endonuclease complex that can cleave both strands of a DNA target sequence typically comprise a Cas protein that has all of its endonuclease domains in a functional state (e.g., wild type endonuclease domains or variants thereof retaining some or all activity in each endonuclease domain). Non-limiting examples of Cas9 nickases suitable for use herein are disclosed in U.S. Patent Appl. Publ. No. 2014/0189896, which is incorporated herein by reference.

Other Cas endonuclease systems have been described in PCT patent applications PCT/US16/32073, filed May 12, 2016 and PCT/US16/32028 filed May 12, 2016, both applications incorporated herein by reference.

"Cas9" (formerly referred to as Cas5, Csn1, or Csx12) herein refers to a Cas endonuclease of a type II CRISPR system that forms a complex with a crNucleotide and a tracrNucleotide, or with a single guide polynucleotide, for specifically recognizing and cleaving all or part of a DNA target sequence. Cas9 protein comprises a RuvC nuclease domain and an HNH (H—N—H) nuclease domain, each of which can cleave a single DNA strand at a target sequence (the concerted action of both domains leads to DNA double-strand cleavage, whereas activity of one domain leads to a nick). In general, the RuvC domain comprises subdomains I, II and III, where domain I is located near the N-terminus of Cas9 and subdomains II and III are located in the middle of the protein, flanking the HNH domain (Hsu et al, Cell 157:1262-1278). A type II CRISPR system includes a DNA cleavage system utilizing a Cas9 endonuclease in complex with at least one polynucleotide component. For example, a Cas9 can be in complex with a CRISPR RNA (crRNA) and a trans-activating CRISPR RNA (tracrRNA). In another example, a Cas9 can be in complex with a single guide RNA.

Any guided endonuclease can be used in the methods disclosed herein. Such endonucleases include, but are not limited to Cas9 and Cpf1 endonucleases. Many endonucleases have been described to date that can recognize specific PAM sequences (see for example—Jinek et al. (2012) Science 337 p 816-821, PCT patent applications PCT/US16/32073, filed May 12, 2016 and PCT/US16/32028 filed May 12, 2016 and Zetsche B et al. 2015. Cell 163, 1013) and cleave the target DNA at a specific position. It is understood that based on the methods and embodiments described herein utilizing a guided Cas system one can now tailor these methods such that they can utilize any guided endonuclease system.

As used herein, the term "guide polynucleotide", relates to a polynucleotide sequence that can form a complex with a Cas endonuclease and enables the Cas endonuclease to recognize, bind to, and optionally cleave a DNA target site. The guide polynucleotide can be a single molecule or a double molecule. The guide polynucleotide sequence can be a RNA sequence, a DNA sequence, or a combination thereof (a RNA-DNA combination sequence). Optionally, the guide polynucleotide can comprise at least one nucleotide, phosphodiester bond or linkage modification such as, but not limited, to Locked Nucleic Acid (LNA), 5-methyl dC, 2,6-Diaminopurine, 2'-Fluoro A, 2'-Fluoro U, 2'-O-Methyl RNA, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotide that solely comprises ribonucleic acids is also referred to as a "guide RNA" or "gRNA" (See also U.S. Patent Application US 2015-0082478 A1, published on Mar. 19, 2015 and US 2015-0059010 A1, published on Feb. 26, 2015, both are hereby incorporated in its entirety by reference).

The guide polynucleotide can also be a single molecule (also referred to as single guide polynucleotide) comprising a crNucleotide sequence linked to a tracrNucleotide sequence. The single guide polynucleotide comprises a first nucleotide sequence domain (referred to as Variable Targeting domain or VT domain) that can hybridize to a nucleotide sequence in a target DNA and a Cas endonuclease recognition domain (CER domain), that interacts with a Cas endonuclease polypeptide. By "domain" it is meant a contiguous stretch of nucleotides that can be RNA, DNA, and/or RNA-DNA-combination sequence. The VT domain and/or the CER domain of a single guide polynucleotide can comprise a RNA sequence, a DNA sequence, or a RNA-DNA-combination sequence. The single guide polynucleotide being comprised of sequences from the crNucleotide and the tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides). The single guide polynucleotide can form a complex with a Cas endonuclease, wherein said guide polynucleotide/Cas endonuclease complex (also referred to as a guide polynucleotide/Cas endonuclease system) can direct the Cas endonuclease to a genomic target site, enabling the Cas endonuclease to recognize, bind to, and optionally nick or cleave (introduce a single or double strand break) the target site. (See also U.S. Patent Application US 2015-0082478 A1, published on Mar. 19, 2015 and US 2015-0059010 A1, published on Feb. 26, 2015, both are hereby incorporated in its entirety by reference.)

The term "variable targeting domain" or "VT domain" is used interchangeably herein and includes a nucleotide sequence that can hybridize (is complementary) to one strand (nucleotide sequence) of a double strand DNA target site. In some embodiments, the variable targeting domain comprises a contiguous stretch of 12 to 30 nucleotides. The variable targeting domain can be composed of a DNA sequence, a RNA sequence, a modified DNA sequence, a modified RNA sequence, or any combination thereof.

The term "Cas endonuclease recognition domain" or "CER domain" (of a guide polynucleotide) is used interchangeably herein and includes a nucleotide sequence that interacts with a Cas endonuclease polypeptide. A CER domain comprises a tracrNucleotide mate sequence followed by a tracrNucleotide sequence. The CER domain can be composed of a DNA sequence, a RNA sequence, a modified DNA sequence, a modified RNA sequence (see for example US 2015-0059010 A1, published on Feb. 26, 2015, incorporated in its entirety by reference herein), or any combination thereof.

The nucleotide sequence linking the crNucleotide and the tracrNucleotide of a single guide polynucleotide can comprise a RNA sequence, a DNA sequence, or a RNA-DNA combination sequence. In one embodiment, the nucleotide sequence linking the crNucleotide and the tracrNucleotide of a single guide polynucleotide can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides in length. In another embodiment, the nucleotide sequence linking the crNucleotide and the tracrNucleotide of a single guide polynucleotide can comprise a tetraloop sequence, such as, but not limiting to a GAAA tetraloop sequence.

The terms "single guide RNA" and "sgRNA" are used interchangeably herein and relate to a synthetic fusion of two RNA molecules, a crRNA (CRISPR RNA) comprising a variable targeting domain (linked to a tracr mate sequence that hybridizes to a tracrRNA), fused to a tracrRNA (transactivating CRISPR RNA). The single guide RNA can comprise a crRNA or crRNA fragment and a tracrRNA or tracrRNA fragment of the type II CRISPR/Cas system that can form a complex with a type II Cas endonuclease, wherein said guide RNA/Cas endonuclease complex can direct the Cas endonuclease to a DNA target site, enabling the Cas endonuclease to recognize, bind to, and optionally nick or cleave (introduce a single or double strand break) the DNA target site.

The terms "guide RNA/Cas endonuclease complex", "guide RNA/Cas endonuclease system", "guide RNA/Cas complex", "guide RNA/Cas system", "gRNA/Cas complex", "gRNA/Cas system", "RNA-guided endonuclease", "RGEN" are used interchangeably herein and refer to at least one RNA component and at least one Cas endonuclease that are capable of forming a complex, wherein said guide RNA/Cas endonuclease complex can direct the Cas endonuclease to a DNA target site, enabling the Cas endonuclease to recognize, bind to, and optionally nick or cleave (introduce a single or double strand break) the DNA target site. A guide RNA/Cas endonuclease complex herein can comprise Cas protein(s) and suitable RNA component(s) of any of the four known CRISPR systems (Horvath and Barrangou, 2010, Science 327:167-170) such as a type I, II, or III CRISPR system. A guide RNA/Cas endonuclease complex can comprise a Type II Cas9 endonuclease and at least one RNA component (e.g., a crRNA and tracrRNA, or a gRNA). (See also U.S. Patent Application US 2015-0082478 A1, published on Mar. 19, 2015 and US 2015-0059010 A1, published on Feb. 26, 2015, both are hereby incorporated in its entirety by reference).

The guide polynucleotide can be introduced into a cell transiently, as single stranded polynucleotide or a double stranded polynucleotide, using any method known in the art such as, but not limited to, particle bombardment, *Agrobacterium* transformation or topical applications. The guide polynucleotide can also be introduced indirectly into a cell by introducing a recombinant DNA molecule (via methods such as, but not limited to, particle bombardment or *Agrobacterium* transformation) comprising a heterologous nucleic acid fragment encoding a guide polynucleotide, operably linked to a specific promoter that is capable of transcribing the guide RNA in said cell. The specific promoter can be, but is not limited to, a RNA polymerase III promoter, which allow for transcription of RNA with precisely defined, unmodified, 5'- and 3'-ends (DiCarlo et al., Nucleic Acids Res. 41: 4336-4343; Ma et al., Mol. Ther. Nucleic Acids 3:e161) as described in WO2016025131, published on Feb. 18, 2016, incorporated herein in its entirety by reference.

The terms "target site", "target sequence", "target site sequence, "target DNA", "target locus", "genomic target site", "genomic target sequence", "genomic target locus" and "protospacer", are used interchangeably herein and refer to a polynucleotide sequence such as, but not limited to, a nucleotide sequence on a chromosome, episome, or any other DNA molecule in the genome (including chromosomal, choloroplastic, mitochondrial DNA, plasmid DNA) of a cell, at which a guide polynucleotide/Cas endonuclease complex can recognize, bind to, and optionally nick or cleave. The target site can be an endogenous site in the genome of a cell, or alternatively, the target site can be heterologous to the cell and thereby not be naturally occurring in the genome of the cell, or the target site can be found in a heterologous genomic location compared to where it occurs in nature. As used herein, terms "endogenous target sequence" and "native target sequence" are used interchangeable herein to refer to a target sequence that is endogenous or native to the genome of a cell and is at the endogenous or native position of that target sequence in the genome of the cell. Cells include, but are not limited to, human, non-human, animal, bacterial, fungal, insect, yeast, non-conventional yeast, and plant cells as well as plants and seeds produced by the methods described herein. An "artificial target site" or "artificial target sequence" are used interchangeably herein and refer to a target sequence that has been introduced into the genome of a cell. Such an artificial target sequence can be identical in sequence to an endogenous or native target sequence in the genome of a cell but be located in a different position (i.e., a non-endogenous or non-native position) in the genome of a cell.

An "altered target site", "altered target sequence", "modified target site", "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

Methods for "modifying a target site" and "altering a target site" are used interchangeably herein and refer to methods for producing an altered target site.

The length of the target DNA sequence (target site) can vary, and includes, for example, target sites that are at least 12, 13, 14, 15, 16, 17, 18, 19, 20, 21, 22, 23, 24, 25, 26, 27, 28, 29, 30 or more nucleotides in length. It is further possible that the target site can be palindromic, that is, the sequence on one strand reads the same in the opposite direction on the complementary strand. The nick/cleavage site can be within the target sequence or the nick/cleavage site could be outside of the target sequence. In another variation, the cleavage could occur at nucleotide positions immediately opposite each other to produce a blunt end cut or, in other Cases, the incisions could be staggered to produce single-stranded overhangs, also called "sticky ends", which can be either 5' overhangs, or 3' overhangs. Active variants of genomic target sites can also be used. Such active variants can comprise at least 65%, 70%, 75%, 80%, 85%, 90%, 91%, 92%, 93%, 94%, 95%, 96%, 97%, 98%, 99% or more sequence identity to the given target site, wherein the active variants retain biological activity and hence are capable of being recognized and cleaved by an Cas endonuclease. Assays to measure the single or double-strand break of a target site by an endonuclease are known in the art and generally measure the overall activity and specificity of the agent on DNA substrates containing recognition sites.

A "protospacer adjacent motif" (PAM) herein refers to a short nucleotide sequence adjacent to a target sequence (protospacer) that is recognized (targeted) by a guide polynucleotide/Cas endonuclease system described herein. The Cas endonuclease may not successfully recognize a target DNA sequence if the target DNA sequence is not followed by a PAM sequence. The sequence and length of a PAM herein can differ depending on the Cas protein or Cas protein complex used. The PAM sequence can be of any length but is typically 1, 2, 3, 4, 5, 6, 7, 8, 9, 10, 11, 12, 13, 14, 15, 16, 17, 18, 19 or 20 nucleotides long.

The terms "targeting", "gene targeting" and "DNA targeting" are used interchangeably herein. DNA targeting herein may be the specific introduction of a knock-out, edit, or knock-in at a particular DNA sequence, such as in a chromosome or plasmid of a cell. In general, DNA targeting can be performed herein by cleaving one or both strands at a specific DNA sequence in a cell with an endonuclease associated with a suitable polynucleotide component. Such DNA cleavage, if a double-strand break (DSB), can prompt NHEJ or HDR processes which can lead to modifications at the target site.

A targeting method herein can be performed in such a way that two or more DNA target sites are targeted in the method, for example. Such a method can optionally be characterized as a multiplex method. Two, three, four, five, six, seven, eight, nine, ten, or more target sites can be targeted at the same time in certain embodiments. A multiplex method is typically performed by a targeting method herein in which multiple different RNA components are provided, each designed to guide an guide polynucleotide/Cas endonuclease complex to a unique DNA target site.

The terms "knock-out", "gene knock-out" and "genetic knock-out" are used interchangeably herein. A knock-out represents a DNA sequence of a cell that has been rendered partially or completely inoperative by targeting with a Cas protein; such a DNA sequence prior to knock-out could have encoded an amino acid sequence, or could have had a regulatory function (e.g., promoter), for example. A knock-out may be produced by an indel (insertion or deletion of nucleotide bases in a target DNA sequence through NHEJ), or by specific removal of sequence that reduces or completely destroys the function of sequence at or near the targeting site.

The guide polynucleotide/Cas endonuclease system can be used in combination with a co-delivered polynucleotide modification template to allow for editing (modification) of a genomic nucleotide sequence of interest. (See also U.S. Patent Application US 2015-0082478 A1, published on Mar. 19, 2015 and WO2015/026886 A1, published on Feb. 26, 2015, both are hereby incorporated in its entirety by reference.)

The terms "knock-in", "gene knock-in, "gene insertion" and "genetic knock-in" are used interchangeably herein. A knock-in represents the replacement or insertion of a DNA sequence at a specific DNA sequence in cell by targeting with a Cas protein (by HR, wherein a suitable donor DNA polynucleotide is also used). Examples of knock-ins are a specific insertion of a heterologous amino acid coding sequence in a coding region of a gene, or a specific insertion of a transcriptional regulatory element in a genetic locus.

Various methods and compositions can be employed to obtain a cell or organism having a polynucleotide of interest inserted in a target site for a Cas endonuclease. Such methods can employ homologous recombination to provide integration of the polynucleotide of Interest at the target site. In one method provided, a polynucleotide of interest is provided to the organism cell in a donor DNA construct. As used herein, "donor DNA" is a DNA construct that comprises a polynucleotide of Interest to be inserted into the target site of a Cas endonuclease. The donor DNA construct further comprises a first and a second region of homology that flank the polynucleotide of Interest. The first and second regions of homology of the donor DNA share homology to a first and a second genomic region, respectively, present in or flanking the target site of the cell or organism genome. By "homology" is meant DNA sequences that are similar. For example, a "region of homology to a genomic region" that is found on the donor DNA is a region of DNA that has a similar sequence to a given "genomic region" in the cell or organism genome. A region of homology can be of any length that is sufficient to promote homologous recombination at the cleaved target site. For example, the region of homology can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800, 5-2900, 5-3000, 5-3100 or more bases in length such that the region of homology has sufficient homology to undergo homologous recombination with the corresponding genomic region. "Sufficient homology" indicates that two polynucleotide sequences have sufficient structural similarity to act as substrates for a homologous recombination reaction. The structural similarity includes overall length of each polynucleotide fragment, as well as the sequence similarity of the polynucleotides. Sequence similarity can be described by the percent sequence identity over the whole length of the sequences, and/or by conserved regions comprising localized similarities such as contiguous nucleotides having 100% sequence identity, and percent sequence identity over a portion of the length of the sequences.

The amount of sequence identity shared by a target and a donor polynucleotide can vary and includes total lengths and/or regions having unit integral values in the ranges of about 1-20 bp, 20-50 bp, 50-100 bp, 75-150 bp, 100-250 bp, 150-300 bp, 200-400 bp, 250-500 bp, 300-600 bp, 350-750 bp, 400-800 bp, 450-900 bp, 500-1000 bp, 600-1250 bp, 700-1500 bp, 800-1750 bp, 900-2000 bp, 1-2.5 kb, 1.5-3 kb, 2-4 kb, 2.5-5 kb, 3-6 kb, 3.5-7 kb, 4-8 kb, 5-10 kb, or up to and including the total length of the target site. These ranges include every integer within the range, for example, the range of 1-20 bp includes 1, 2, 3, 4, 5, 6, 7, 8, 9, 10, 11, 12, 13, 14, 15, 16, 17, 18, 19 and 20 bps. The amount of homology can also be described by percent sequence identity over the full aligned length of the two polynucleotides which includes percent sequence identity of about at least 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. Sufficient homology includes any combination of polynucleotide length, global percent sequence identity, and optionally conserved regions of contiguous nucleotides or local percent sequence identity, for example sufficient homology can be described as a region of 75-150 bp having at least 80% sequence identity to a region of the target locus. Sufficient homology can also be described by the predicted ability of two polynucleotides to specifically hybridize under high stringency conditions, see, for example, Sambrook et al., (1989) Molecular Cloning: A Laboratory Manual, (Cold Spring Harbor Laboratory Press, NY); Current Protocols in Molecular Biology, Ausubel et al., Eds (1994) Current Protocols, (Greene Publishing Associates, Inc. and John Wiley & Sons, Inc.); and, Tijssen (1993) Laboratory Techniques in Biochemistry and Molecular Biology—Hybridization with Nucleic Acid Probes, (Elsevier, New York).

The structural similarity between a given genomic region and the corresponding region of homology found on the donor DNA can be any degree of sequence identity that allows for homologous recombination to occur. For example, the amount of homology or sequence identity shared by the "region of homology" of the donor DNA and the "genomic region" of the organism genome can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination The region of homology on the donor DNA can have homology to any sequence flanking the target site. While in some embodiments the regions of homology share significant sequence homology to the genomic sequence immediately flanking the target site, it is recognized that the regions of homology can be designed to have sufficient homology to regions that may be further 5' or 3' to the target site. In still other embodiments, the regions of homology can also have homology with a fragment of the target site along with downstream genomic regions. In one embodiment, the first region of homology further comprises a first fragment of the target site and the second region of homology comprises a second fragment of the target site, wherein the first and second fragments are dissimilar.

As used herein, "homologous recombination" includes the exchange of DNA fragments between two DNA molecules at the sites of homology.

Further uses for guide RNA/Cas endonuclease systems have been described (See U.S. Patent Application US 2015-0082478 A1, published on Mar. 19, 2015, WO2015/026886 A1, published on Feb. 26, 2015, US 2015-0059010 A1, published on Feb. 26, 2015, U.S. application 62/023,246, filed on Jul. 7, 2014, and U.S. application 62/036,652, filed on Aug. 13, 2014, all of which are incorporated by reference herein) and include but are not limited to modifying or replacing nucleotide sequences of interest (such as a regulatory elements), insertion of polynucleotides of interest, gene knock-out, gene-knock in, modification of splicing sites and/or introducing alternate splicing sites, modifications of nucleotide sequences encoding a protein of interest, amino acid and/or protein fusions, and gene silencing by expressing an inverted repeat into a gene of interest.

In certain embodiments, through genome editing approaches described herein and those available to one of ordinary skill in the art, specific motifs of one or more regulatory elements of the EMEs disclosed herein can be engineered to modulate the expression of one or more host plant endogenous genes.

Methods for transforming dicots, primarily by use of *Agrobacterium tumefaciens*, and obtaining transgenic plants have been published, among others, for cotton (U.S. Pat. Nos. 5,004,863, 5,159,135); soybean (U.S. Pat. Nos. 5,569,834, 5,416,011); *Brassica* (U.S. Pat. No. 5,463,174); peanut (Cheng et al., Plant Cell Rep. 15:653-657 (1996), McKently et al., Plant Cell Rep. 14:699-703 (1995)); papaya (Ling et al., Bio/technology 9:752-758 (1991)); and pea (Grant et al., Plant Cell Rep. 15:254-258 (1995)). For a review of other commonly used methods of plant transformation see Newell, C. A., Mol. Biotechnol. 16:53-65 (2000). One of these methods of transformation uses *Agrobacterium rhizogenes* (Tepfler, M. and Casse-Delbart, F., Microbiol. Sci. 4:24-28 (1987)). Transformation of soybeans using direct delivery of DNA has been published using PEG fusion (PCT Publication No. WO 92/17598), electroporation (Chowrira et al., Mol. Biotechnol. 3:17-23 (1995); Christou et al., Proc. Natl. Acad. Sci. U.S.A. 84:3962-3966 (1987)), microinjection, or particle bombardment (McCabe et al., Biotechnology 6:923-926 (1988); Christou et al., Plant Physiol. 87:671-674 (1988)).

There are a variety of methods for the regeneration of plants from plant tissues. The particular method of regeneration will depend on the starting plant tissue and the particular plant species to be regenerated. The regeneration, development and cultivation of plants from single plant protoplast transformants or from various transformed explants is well known in the art (Weissbach and Weissbach, Eds.; In Methods for Plant Molecular Biology; Academic Press, Inc.: San Diego, CA, 1988). This regeneration and growth process typically includes the steps of selection of transformed cells, culturing those individualized cells through the usual stages of embryonic development or through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present disclosure containing a desired polypeptide is cultivated using methods well known to one skilled in the art.

EXAMPLES

The present disclosure is further defined in the following Examples, in which parts and percentages are by weight and degrees are Celsius, unless otherwise stated. Sequences of promoters, cDNA, adaptors, and primers listed in this disclosure all are in the 5' to 3' orientation unless described otherwise. It should be understood that these Examples, while indicating preferred embodiments of the disclosure, are given by way of illustration only. From the above discussion and these Examples, one skilled in the art can ascertain the essential characteristics of this disclosure, and without departing from the spirit and scope thereof, can make various changes and modifications of the disclosure to adapt it to various usages and conditions. Thus, various modifications of the disclosure in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Effect of the EMEs on Gene Expression

Expression modulating elements (EMEs) were identified and appropriate transformation vectors with a reporter gene (e.g., GUS) were constructed. The EMEs were evaluated on 30-60 day old plant leaf samples from transformed *Arabidopsis* for their expression modulation.

The EMEs were evaluated as 1× repeats cloned upstream of the AtGOS2 promoter operably linked to the GUS reporter gene. The AtGOS2 promoter operably linked to the GUS reporter gene in the absence of an EME was used as a control. *Arabadopsis* plants were transformed using the floral dip procedure (Clough and Bent, 1998). Briefly, about 4-week old *Arabidopsis* plants with floral buds were dipped in a bacterial suspension of Abrobacterium strain C58 cultured in YEP medium comprising 5% (w/v) sucrose and 0.05% (v/v) Silwet-77 (Mohanyt et al. 2009). The transformed seeds were generated by screening through BASTA (10 µg/ml) selection. GUS staining and expression was performed according to the methods described in Jefferson et al. (*EMBO Journal*, 6(13): 3901-3907 (1987)). Specifically, GUS expression was measured in a fluorometric assay with 4-methyl umbelliferyl glucuronide (MUG) used as the substrate.

As shown in Table 2, EMEs comprising SEQ ID NOs: 1 and 10-14 increased expression of the GUS reporter gene compared to the control, while SEQ ID NOs: 2-9 decreased expression of the GUS reporter gene compared to the control.

These results demonstrate that the tested EMEs modulate the expression of target genes.

TABLE 2

Effects of EMEs on Moderate Constitutive Plant Promoter

| SEQ ID NO | EME name | Single copy events | Avg. MUG value with SE | Fold Change |
|---|---|---|---|---|
| SEQ ID NO: 1 | 1X-SF-Os-ENHs-4-1 | 7 | 222795 ± 9993 | 1.22 |
| SEQ ID NO: 2 | 1X-SF-At-ENH_9 | 14 | 146014 ± 9304 | 0.8 |
| SEQ ID NO: 3 | 1X-SF-At-ENH_23 | 6 | 145392 ± 9577 | 0.8 |
| SEQ ID NO: 4 | 1X-SF-At-ENH_25-1 | 9 | 157560 ± 9523 | 0.87 |
| SEQ ID NO: 5 | 1X-SF-At-ENH_25-2 | 3 | 160940 ± 12670 | 0.88 |
| SEQ ID NO: 6 | 1X-SF-At-ENH_25-3 | 5 | 171998 ± 15036 | 0.95 |
| SEQ ID NO: 7 | 1X-SF-Os-ENHs-1-1 | 7 | 142068 ± 11280 | 0.78 |
| SEQ ID NO: 8 | 1X-SF-Os-ENHs-1-2 | 5 | 172220 ± 11125 | 0.95 |
| SEQ ID NO: 9 | 1X-SF-At-ENH_1 | 8 | 156011 ± 8662 | 0.86 |
| SEQ ID NO: 10 | 1X-SF-Os-ENHs-4-2 | 3 | 222720 ± 12698 | 1.22 |
| SEQ ID NO: 11 | 1X-SF-Os-ENHs-28-1 | 13 | 248535 ± 15770 | 1.37 |
| SEQ ID NO: 12 | 1X-CP-MF-At-ENH-13-1 | 16 | 237793 ± 10310 | 1.31 |
| SEQ ID NO: 13 | 1X-CP-MF-At-ENH-21 | 5 | 234689 ± 11007 | 1.29 |
| SEQ ID NO: 14 | 1X-SF-Os-ENHs-12 | 7 | 256578 ± 18487 | 1.41 |
|  | At-GOS2 Promoter | 6 | 181768 ± 5352 | 1 |

Example 2

Effect of the EMEs on Developmental Stage and Tissue Specific Expression

The EMEs that showed elevated expression (SEQ ID NO: 9-14) were further evaluated at a different development stage (60-day old plants) and in different tissues i.e. leaves (Table 3) and stems (Table 4) for understanding the spatial and temporal expression pattern. All of the EMEs showed consistently elevated expression levels compared to vector control.

TABLE 3

Effects of EMEs on Expression in Leaves

| SEQ ID NO: | EME name | Single copy events | Avg. MUG value with SE | Fold Change |
|---|---|---|---|---|
| SEQ ID NO: 1 | 1X-SF-Os-ENHs-4-1 | 7 | 227820 ± 27020 | 1.33 |
| SEQ ID NO: 10 | 1X-SF-Os-ENHs-4-2 | 3 | 228021 ± 22170 | 1.33 |
| SEQ ID NO: 11 | 1X-SF-Os-ENHs-28-1 | 13 | 230788 ± 9079 | 1.35 |

TABLE 3-continued

Effects of EMEs on Expression in Leaves

| SEQ ID NO: | EME name | Single copy events | Avg. MUG value with SE | Fold Change |
|---|---|---|---|---|
| SEQ ID NO: 12 | 1X-CP-MF-At-ENH-13-1 | 16 | 197247 ± 9028 | 1.15 |
| SEQ ID NO: 13 | 1X-CP-MF-At-ENH-21 | 5 | 260526 ± 25121 | 1.52 |
| SEQ ID NO: 14 | 1X-SF-Os-ENHs-12 | 7 | 194756 ± 11814 | 1.14 |
|  | At-GOS2 Promoter | 6 | 171010 ± 7702 | 1 |

TABLE 4

Effects of EMEs on Expression in Stems

| SEQ ID NO: | EME name | Single copy events | Avg. MUG value with SE | Fold Change |
|---|---|---|---|---|
| SEQ ID NO: 1 | 1X-SF-Os-ENHs-4-1 | 7 | 203080 ± 13245 | 1.46 |
| SEQ ID NO: 10 | 1X-SF-Os-ENHs-4-2 | 3 | 196227 ± 29593 | 1.41 |
| SEQ ID NO: 11 | 1X-SF-Os-ENHs-28-1 | 13 | 166380 ± 12430 | 1.12 |
| SEQ ID NO: 12 | 1X-CP-MF-At-ENH-13-1 | 16 | 181636 ± 14567 | 1.31 |
| SEQ ID NO: 13 | 1X-CP-MF-At-ENH-21 | 5 | 258110 ± 23147 | 1.86 |
| SEQ ID NO: 14 | 1X-SF-Os-ENHs-12 | 7 | 141316 ± 13759 | 1.02 |
|  | At-GOS2 Promoter | 6 | 138668 ± 14118 | 1 |

Example 3

Transient Evaluation of EMEs in Rice Callus

The EMEs were evaluated in rice callus to understand the translatability of these elements for their expression modulation. The EMEs were evaluated as 1× repeats cloned upstream of the minimal 35S promoter operably linked to the GUS reporter gene. The minimal 35S promoter operably linked to the GUS reporter gene in the absence of an EME was used as a control.

Briefly, rice callus was generated from *O. sativa* spp. *indica* rice var. IRV95 seeds. The rice callus was then transiently transfected via biolistic particle delivery with a vector comprising an EME cloned upstream of the minimal 35S promoter operably linked to the GUS reporter gene or a vector comprising the minimal 35S promoter operably linked to the GUS reporter gene in the absence of an EME (control).

As shown in FIG. 1, rice callus transfected with a vector comprising an EME have increased GUS expression compared to the control rice callus. The expression results shown in rice callus correlate with the expression results shown in *Arabidopsis*, thereby indicating that these EMEs can modulate expression of genes operably linked to multiple types of promoters in multiple plant species.

Example 4

Maize Protoplast Assay and Quantification of Reporter Gene

Transformation vectors with a reporter gene (e.g., ZsGreen) operably linked to an EME were constructed. Those vectors were tested in maize leaf protoplasts. The protoplast expression assay uses a modified version of this commonly used protocol to facilitate the delivery of known plasmid DNA to cells isolated from maize inbred leaf mesophyll cells. The transfection method utilized in this assay is polyethelene glycol 40% w/v mediated transfection.

The quantification methodology used in the protoplast expression assay is based around the BioTek Cytation5 inverted microscope imager. Images are taken of the transfected protoplast populations using excitation and emission spectra as determined based on the fluorescent markers chosen for the experiment. When quantification of a known element is required, a dual cassette expression vector is used. The normalization cassette consists of a strong constitutive promoter Seteria UBI along with Seteria UBI intron driving TagRFP; this cassette also acts as a transfection control to monitor transfection efficiency. The experimental cassette contains the DNA sequence being evaluated with ZsGreen as the reporter gene. Post imaging processing is carried out primarily using the BioTek Gen5 software. Using circularity, size, and presence of TagRFP fluorescence algorithm, positively transfected cells were identified, and the relative fluorescence based on pixel intensity was recorded. The fluorescence recorded from the GFP channel is normalized to the RFP in order to quantify on a cell by cell basis. The harmonic mean is calculated for each experimental entity and compared to the appropriate control to determine significance based on a p value <0.5 even though in most cases significance was established at a higher stringency (p value<0.0001). In other cases, the geometric mean is calculated for each experimental entity and ANOVA was done using Tukey with an alpha value of 5%.

Example 5

Effect of the EMEs on Gene Expression in Maize Protoplast Assay

Fourteen EME sequences were tested as 3× multimers upstream of the minimal CAMV35S promoter (CAMV35S (MIN)) in maize protoplasts. The CAMV35S promoter served as the control. Expression data from this experiment is shown in Table 5 below. UBI1ZM PRO, ZM-ADF4 PRO, and ZM-GOS2 PRO serve as references for High, Low, and medium levels of expression.

The results from these studies show that 5 of the EMEs tested produced expression levels that were above the level of the control (i.e., no EME), with the increase in expression ranging from 1.45-3.32×.

TABLE 5

Effects of EMEs on Expression in Maize Protoplasts

| EME SEQ ID NO: | EME | EME Multimer | Promoter | Fold Increase over Control |
|---|---|---|---|---|
| — | None | — | CAMV35S (MIN) | 1.00 |
| SEQ ID NO: 1 | 1X-SF-Os-ENHs-4-1 | 3X | CAMV35S (MIN) | 3.04 |
| SEQ ID NO: 2 | 1X-SF-At-ENH_9 | 3X | CAMV35S (MIN) | 0.63 |
| SEQ ID NO: 3 | 1X-SF-At-ENH_23 | 3X | CAMV35S (MIN) | 0.61 |
| SEQ ID NO: 4 | 1X-SF-At-ENH_25-1 | 3X | CAMV35S (MIN) | 0.68 |
| SEQ ID NO: 5 | 1X-SF-At-ENH_25-2 | 3X | CAMV35S (MIN) | 0.78 |
| SEQ ID NO: 6 | 1X-SF-At-ENH_25-3 | 3X | CAMV35S (MIN) | 0.69 |
| SEQ ID NO: 7 | 1X-SF-Os-ENHs-1-1 | 3X | CAMV35S (MIN) | 0.07 |
| SEQ ID NO: 8 | 1X-SF-Os-ENHs-1-2 | 3X | CAMV35S (MIN) | 0.42 |
| SEQ ID NO: 9 | 1X-SF-At-ENH_1 | 3X | CAMV35S (MIN) | 0.70 |
| SEQ ID NO: 10 | 1X-SF-Os-ENHs-4-2 | 3X | CAMV35S (MIN) | 0.68 |
| SEQ ID NO: 11 | 1X-SF-Os-ENHs-28-1 | 3X | CAMV35S (MIN) | 2.46 |
| SEQ ID NO: 12 | 1X-CP-MF-At-ENH-13-1 | 3X | CAMV35S (MIN) | 2.69 |
| SEQ ID NO: 13 | 1X-CP-MF-At-ENH-21 | 3X | CAMV35S (MIN) | 1.45 |
| SEQ ID NO: 14 | 1X-SF-Os-ENHs-12 | 3X | CAMV35S (MIN) | 3.32 |

Example 6

Maize Protoplast Assay and Quantification of Reporter Gene

A set of constructs was created using the EMEs as 2× multimers in the context of the full ZM-GOS2 PRO, which is a constitutive promoter with moderate strength. The EME multimers were inserted 20 bases upstream of the TATA box. These constructs were created using the 5 EMEs that produced an increase in the CAMV35S minimal promoter context and one additional EME from this group that did not produce an increase. UBI1ZM PRO, and ZM-ADF4 PRO serve as references for high, and low levels of expression. The native ZM-GOS2 PRO serves as the control.

The results from this study show that, in the context of a full length ZM-GOS2 PRO, SF-Os-ENHs-4-1 shows a 2× increase in expression over that of the control. The other 5 EMEs tested do no show an increase in this experiment.

TABLE 6

Effects of EMEs on Expression in Maize Protoplasts

| EME SEQ ID NO: | EME | EME Multimer | Promoter | Fold increase over control |
|---|---|---|---|---|
| SEQ ID NO: 7 | 1X-SF-Os-ENHs-1-1 | 2X | ZM-GOS2 PRO | 0.79 |
| SEQ ID NO: 1 | 1X-SF-Os-ENHs-4-1 | 2X | ZM-GOS2 PRO | 1.99 |
| SEQ ID NO: 11 | 1X-SF-Os-ENHs-28-1 | 2X | ZM-GOS2 PRO | 0.68 |
| SEQ ID NO: 12 | 1X-CP-MF-At-ENH-13-1 | 2X | ZM-GOS2 PRO | 0.82 |
| SEQ ID NO: 13 | 1X-CP-MF-At-ENH-21 | 2X | ZM-GOS2 PRO | 0.89 |
| SEQ ID NO: 14 | 1X-SF-Os-ENHs-12 | 2X | ZM-GOS2 PRO | 0.91 |

What is claimed is:

1. A plant cell comprising at least one copy of an expression modulating element operably linked to a polynucleotide, the expression modulating element consisting essentially of a nucleic acid sequence having at least 98% sequence identity to SEQ ID NO: 1, and the polynucleotide comprising a promoter, the promoter heterologous to the expression modulating element, and a gene of interest or a functional RNA, wherein expression of the gene of interest or functional RNA is increased as compared to a control plant cell not comprising the expression modulating element.

2. The plant cell of claim 1, wherein the plant cell comprises two to ten copies of the expression modulating element operably linked to the polynucleotide.

3. A plant comprising the plant cell of claim 1.

4. The plant of claim 3, wherein the plant is maize, soybean, rice, wheat, sunflower, cotton, sorghum or canola.

5. A seed produced by the plant of claim 3, wherein the seed comprises the expression modulating element.

6. A method of increasing the expression of an endogenous gene or a functional RNA of a plant, the method comprising introducing at least one copy of an expression modulating element, the expression modulating element consisting essentially of a nucleic acid sequence having at least 98% sequence identity to SEQ ID NO: 1, operably linked to a polynucleotide comprising a promoter, the promoter heterologous to the expression modulating element, and the endogenous gene or the endogenous functional RNA, wherein expression of the endogenous gene or the endogenous functional RNA is increased as compared to a control plant cell not comprising the expression modulating element.

7. The method of claim 6, wherein the expression modulating element is introduced upstream of the promoter of the endogenous gene or the functional RNA.

8. The method of claim 6, wherein the expression modulating element is introduced through genome editing.

9. The method of claim 8, wherein the genome editing is performed through guided Cas9 endonuclease.

10. The method of claim 6, wherein the expression modulating element is operably linked to a heterologous promoter sequence and an intron.

11. The method of claim 6, wherein the plant is maize, soybean, rice, wheat, sorghum, or canola.

12. The method of claim 6, wherein the endogenous gene is selected from the group consisting of a reporter gene, a disease resistance gene, a herbicide resistance gene, an insect resistance gene; a gene involved in carbohydrate metabolism, a gene involved in fatty acid metabolism, a gene involved in amino acid metabolism, a gene involved in plant development, a gene involved in plant growth regulation, a gene involved in yield improvement, a gene involved in drought resistance, a gene involved in increasing nutrient utilization efficiency, a gene involved in cold resistance, a gene involved in heat resistance and a gene involved in salt resistance in plants.

13. The method of claim 6, wherein the functional RNA is a microRNA or a microRNA precursor.

14. The plant cell of claim 1, wherein the gene of interest encodes a polypeptide conferring herbicide tolerance, insect resistance, disease resistance, or abiotic stress tolerance.

15. The plant cell of claim 1, wherein the functional RNA is a microRNA or a microRNA precursor.

* * * * *

SEQUENCE LISTING

<160> NUMBER OF SEQ ID NOS: 100

<210> SEQ ID NO 1
<211> LENGTH: 31
<212> TYPE: DNA
<213> ORGANISM: Oryza sativa

<400> SEQUENCE: 1
gtcggccgag cggcgggatc ggtggggaca c          31

<210> SEQ ID NO 2
<211> LENGTH: 30
<212> TYPE: DNA
<213> ORGANISM: Arabidopsis thaliana

<400> SEQUENCE: 2
taattcaaga caaggaaaaa aaaacgaaag            30

```
<210> SEQ ID NO 3
<211> LENGTH: 31
<212> TYPE: DNA
<213> ORGANISM: Arabidopsis thaliana

<400> SEQUENCE: 3
atcgtaatct cagcccaata ccctattttc c                          31

<210> SEQ ID NO 4
<211> LENGTH: 31
<212> TYPE: DNA
<213> ORGANISM: Arabidopsis thaliana

<400> SEQUENCE: 4
agccaatgag tgataatccg gtgaaacgca t                          31

<210> SEQ ID NO 5
<211> LENGTH: 31
<212> TYPE: DNA
<213> ORGANISM: Arabidopsis thaliana

<400> SEQUENCE: 5
ccccactttt cctccatacc tcactacacc c                          31

<210> SEQ ID NO 6
<211> LENGTH: 31
<212> TYPE: DNA
<213> ORGANISM: Arabidopsis thaliana

<400> SEQUENCE: 6
agtacgttac gaaaccaaat aaaaacaatc a                          31

<210> SEQ ID NO 7
<211> LENGTH: 31
<212> TYPE: DNA
<213> ORGANISM: Oryza sativa

<400> SEQUENCE: 7
agggcccacg tgtccccatt cccactcctg t                          31

<210> SEQ ID NO 8
<211> LENGTH: 31
<212> TYPE: DNA
<213> ORGANISM: Oryza sativa

<400> SEQUENCE: 8
gatgggaggg agacagcagc tcagcaatgg c                          31

<210> SEQ ID NO 9
<211> LENGTH: 30
<212> TYPE: DNA
<213> ORGANISM: Arabidopsis thaliana

<400> SEQUENCE: 9
aatgatgaat ctgaacatgt agtcaatgac                            30

<210> SEQ ID NO 10
<211> LENGTH: 31
<212> TYPE: DNA
<213> ORGANISM: Oryza sativa

<400> SEQUENCE: 10
catgtgggga cgaaattacg tgggggaccc a                          31
```

<210> SEQ ID NO 11
<211> LENGTH: 31
<212> TYPE: DNA
<213> ORGANISM: Oryza sativa

<400> SEQUENCE: 11
ggagaacagt gacagtggca gcagtgcgcg t        31

<210> SEQ ID NO 12
<211> LENGTH: 44
<212> TYPE: DNA
<213> ORGANISM: Arabidopsis thaliana

<400> SEQUENCE: 12
atttgtcgga tctatcatgg tctccattaa gtaaaatata ttca        44

<210> SEQ ID NO 13
<211> LENGTH: 46
<212> TYPE: DNA
<213> ORGANISM: Arabidopsis thaliana

<400> SEQUENCE: 13
ctttcaaaaa agtattgggt ttttttttcca gttttgggcc ccacat        46

<210> SEQ ID NO 14
<211> LENGTH: 51
<212> TYPE: DNA
<213> ORGANISM: Oryza sativa

<400> SEQUENCE: 14
agtgtagcac catgtgacca tgtcttctat ggcgcatagc ccagacaagt c        51

<210> SEQ ID NO 15
<211> LENGTH: 30
<212> TYPE: DNA
<213> ORGANISM: Oryza sativa

<400> SEQUENCE: 15
actgattaaa gaagggacgc aaagcagact        30

<210> SEQ ID NO 16
<211> LENGTH: 30
<212> TYPE: DNA
<213> ORGANISM: Oryza sativa

<400> SEQUENCE: 16
aatcgggccg aggaaatgaa gcccggcaag        30

<210> SEQ ID NO 17
<211> LENGTH: 30
<212> TYPE: DNA
<213> ORGANISM: Oryza sativa

<400> SEQUENCE: 17
gctgggcttc tacttcttgg cccgattgaa        30

<210> SEQ ID NO 18
<211> LENGTH: 30
<212> TYPE: DNA
<213> ORGANISM: Oryza sativa

<400> SEQUENCE: 18

```
gcacgcgcag tgcacgtagc gatttcacct                              30

<210> SEQ ID NO 19
<211> LENGTH: 30
<212> TYPE: DNA
<213> ORGANISM: Oryza sativa

<400> SEQUENCE: 19
gcgcaaggga ggtaaactag acttttctgc                              30

<210> SEQ ID NO 20
<211> LENGTH: 30
<212> TYPE: DNA
<213> ORGANISM: Oryza sativa

<400> SEQUENCE: 20
cggactcctc gtgcgcacgt ccttcctgcc                              30

<210> SEQ ID NO 21
<211> LENGTH: 30
<212> TYPE: DNA
<213> ORGANISM: Oryza sativa

<400> SEQUENCE: 21
agaaagaaag agaaggggggg gagctcggct                             30

<210> SEQ ID NO 22
<211> LENGTH: 30
<212> TYPE: DNA
<213> ORGANISM: Oryza sativa

<400> SEQUENCE: 22
ggcataggtt agggattatg tagatccaac                              30

<210> SEQ ID NO 23
<211> LENGTH: 30
<212> TYPE: DNA
<213> ORGANISM: Oryza sativa

<400> SEQUENCE: 23
ttgattggtg attgaattga tggatggggg                              30

<210> SEQ ID NO 24
<211> LENGTH: 30
<212> TYPE: DNA
<213> ORGANISM: Oryza sativa

<400> SEQUENCE: 24
cagggaggca aaacagactt ttgtctgggc                              30

<210> SEQ ID NO 25
<211> LENGTH: 30
<212> TYPE: DNA
<213> ORGANISM: Oryza sativa

<400> SEQUENCE: 25
acctggtagg ccgtgccgct gacgtgtggg                              30

<210> SEQ ID NO 26
<211> LENGTH: 30
<212> TYPE: DNA
<213> ORGANISM: Oryza sativa

<400> SEQUENCE: 26
```
aggtggggcc agatgtgctg tggcccacct                                      30

<210> SEQ ID NO 27
<211> LENGTH: 30
<212> TYPE: DNA
<213> ORGANISM: Oryza sativa

<400> SEQUENCE: 27
gtggcgacac aaggcgatga ggtggcactg                                      30

<210> SEQ ID NO 28
<211> LENGTH: 30
<212> TYPE: DNA
<213> ORGANISM: Oryza sativa

<400> SEQUENCE: 28
aggggaaggg gccaagccgg gccgaggcaa                                      30

<210> SEQ ID NO 29
<211> LENGTH: 30
<212> TYPE: DNA
<213> ORGANISM: Oryza sativa

<400> SEQUENCE: 29
ctgagaggag aggaggcggc tcaggttggg                                      30

<210> SEQ ID NO 30
<211> LENGTH: 30
<212> TYPE: DNA
<213> ORGANISM: Oryza sativa

<400> SEQUENCE: 30
ggctgaaaac aaagcaaaga aagaaagaga                                      30

<210> SEQ ID NO 31
<211> LENGTH: 30
<212> TYPE: DNA
<213> ORGANISM: Oryza sativa

<400> SEQUENCE: 31
ccaaagatac cgggcccaca cagctgaccg                                      30

<210> SEQ ID NO 32
<211> LENGTH: 30
<212> TYPE: DNA
<213> ORGANISM: Oryza sativa

<400> SEQUENCE: 32
gccaggtcgc catccgtttg ctcaggccag                                      30

<210> SEQ ID NO 33
<211> LENGTH: 30
<212> TYPE: DNA
<213> ORGANISM: Oryza sativa

<400> SEQUENCE: 33
gccctgcacg tcaacgacac aaggggacgg                                      30

<210> SEQ ID NO 34
<211> LENGTH: 30
<212> TYPE: DNA
<213> ORGANISM: Oryza sativa

<400> SEQUENCE: 34
actagacttt tggatggctg agaggagagg                                              30

<210> SEQ ID NO 35
<211> LENGTH: 30
<212> TYPE: DNA
<213> ORGANISM: Oryza sativa

<400> SEQUENCE: 35
tgagaggaga ggaggcggct caggttgggc                                              30

<210> SEQ ID NO 36
<211> LENGTH: 30
<212> TYPE: DNA
<213> ORGANISM: Oryza sativa

<400> SEQUENCE: 36
aaagtctgat ttacctccct ggcgctacag                                              30

<210> SEQ ID NO 37
<211> LENGTH: 30
<212> TYPE: DNA
<213> ORGANISM: Oryza sativa

<400> SEQUENCE: 37
ccttctgcca cctggacagc aaactttatt                                              30

<210> SEQ ID NO 38
<211> LENGTH: 30
<212> TYPE: DNA
<213> ORGANISM: Oryza sativa

<400> SEQUENCE: 38
agtgcttgga agtagaagcc cagccgaaag                                              30

<210> SEQ ID NO 39
<211> LENGTH: 30
<212> TYPE: DNA
<213> ORGANISM: Oryza sativa

<400> SEQUENCE: 39
cacccgggcc cactgtacgt caccccatcc                                              30

<210> SEQ ID NO 40
<211> LENGTH: 30
<212> TYPE: DNA
<213> ORGANISM: Oryza sativa

<400> SEQUENCE: 40
agactttcgt cttgagctgg ctgaaaaaca                                              30

<210> SEQ ID NO 41
<211> LENGTH: 30
<212> TYPE: DNA
<213> ORGANISM: Oryza sativa

<400> SEQUENCE: 41
ccctaaaccc taaaccctaa accctaaacc                                              30

<210> SEQ ID NO 42
<211> LENGTH: 30
<212> TYPE: DNA
<213> ORGANISM: Oryza sativa

```
<400> SEQUENCE: 42
tcccgaaccg ctgcatcctg gccgtccatc                              30

<210> SEQ ID NO 43
<211> LENGTH: 30
<212> TYPE: DNA
<213> ORGANISM: Oryza sativa

<400> SEQUENCE: 43
tgtatggtag actattcctt tgggttgggc                              30

<210> SEQ ID NO 44
<211> LENGTH: 30
<212> TYPE: DNA
<213> ORGANISM: Oryza sativa

<400> SEQUENCE: 44
tggggacctt tgcacagatt tttcctcgcc                              30

<210> SEQ ID NO 45
<211> LENGTH: 30
<212> TYPE: DNA
<213> ORGANISM: Oryza sativa

<400> SEQUENCE: 45 tttttcccett tcttggacct tttgtgtaga                             30

<210> SEQ ID NO 46
<211> LENGTH: 30
<212> TYPE: DNA
<213> ORGANISM: Oryza sativa

<400> SEQUENCE: 46
aaagatgtcg attcagtgga cccttgcttg                              30

<210> SEQ ID NO 47
<211> LENGTH: 30
<212> TYPE: DNA
<213> ORGANISM: Oryza sativa

<400> SEQUENCE: 47
tctttcacga gatggggccg gcaccattag                              30

<210> SEQ ID NO 48
<211> LENGTH: 30
<212> TYPE: DNA
<213> ORGANISM: Oryza sativa

<400> SEQUENCE: 48
accacaacag catatatcta cgtgcatatt                              30

<210> SEQ ID NO 49
<211> LENGTH: 30
<212> TYPE: DNA
<213> ORGANISM: Oryza sativa

<400> SEQUENCE: 49
atattttatg tttgtttcgg aaacttcccc                              30

<210> SEQ ID NO 50
<211> LENGTH: 30
<212> TYPE: DNA
```

```
<213> ORGANISM: Oryza sativa

<400> SEQUENCE: 50
actacacgta ggccatcttg ctgtggggca                               30

<210> SEQ ID NO 51
<211> LENGTH: 30
<212> TYPE: DNA
<213> ORGANISM: Oryza sativa

<400> SEQUENCE: 51
taaactagac ttttctgccg gctgagagga                               30

<210> SEQ ID NO 52
<211> LENGTH: 30
<212> TYPE: DNA
<213> ORGANISM: Oryza sativa

<400> SEQUENCE: 52
gagctcggct gggctgactt gggctgcacg                               30

<210> SEQ ID NO 53
<211> LENGTH: 30
<212> TYPE: DNA
<213> ORGANISM: Oryza sativa

<400> SEQUENCE: 53
gcacgtcctt cctgcctcat gcatgggcca                               30

<210> SEQ ID NO 54
<211> LENGTH: 30
<212> TYPE: DNA
<213> ORGANISM: Oryza sativa

<400> SEQUENCE: 54
ctcggcccac caagccaggt cgccatccgt                               30

<210> SEQ ID NO 55
<211> LENGTH: 30
<212> TYPE: DNA
<213> ORGANISM: Oryza sativa

<400> SEQUENCE: 55
tcttgggctg gctgaaaaca aagcaaagaa                               30

<210> SEQ ID NO 56
<211> LENGTH: 30
<212> TYPE: DNA
<213> ORGANISM: Oryza sativa

<400> SEQUENCE: 56
tttgcgtacc tcctttaatc agtgcttgga                               30

<210> SEQ ID NO 57
<211> LENGTH: 30
<212> TYPE: DNA
<213> ORGANISM: Oryza sativa

<400> SEQUENCE: 57
aaccgtcgcc gccgcccccct cctctcggga                              30

<210> SEQ ID NO 58
<211> LENGTH: 30
```

<212> TYPE: DNA
<213> ORGANISM: Oryza sativa

<400> SEQUENCE: 58
cgactcggag cccagttacg ctgggctgtt             30

<210> SEQ ID NO 59
<211> LENGTH: 30
<212> TYPE: DNA
<213> ORGANISM: Oryza sativa

<400> SEQUENCE: 59
agagggaaga ggagggagag agaggctgcg             30

<210> SEQ ID NO 60
<211> LENGTH: 30
<212> TYPE: DNA
<213> ORGANISM: Oryza sativa

<400> SEQUENCE: 60
cgtgccatgc ttaaaccggg ccaaatctcc             30

<210> SEQ ID NO 61
<211> LENGTH: 30
<212> TYPE: DNA
<213> ORGANISM: Oryza sativa

<400> SEQUENCE: 61
cacctggaca gcaaacttta ttaagagtct             30

<210> SEQ ID NO 62
<211> LENGTH: 30
<212> TYPE: DNA
<213> ORGANISM: Oryza sativa

<400> SEQUENCE: 62
gggaggtcaa acagacttta tctgggctga             30

<210> SEQ ID NO 63
<211> LENGTH: 30
<212> TYPE: DNA
<213> ORGANISM: Oryza sativa

<400> SEQUENCE: 63
aacagacttt atctgggctg agaggaaggg             30

<210> SEQ ID NO 64
<211> LENGTH: 30
<212> TYPE: DNA
<213> ORGANISM: Oryza sativa

<400> SEQUENCE: 64
tggggcccac attgcggttc aggcaatcag             30

<210> SEQ ID NO 65
<211> LENGTH: 30
<212> TYPE: DNA
<213> ORGANISM: Oryza sativa

<400> SEQUENCE: 65
gtccaatcat cccgaaccgc tgcatcctgg             30

<210> SEQ ID NO 66

```
<211> LENGTH: 30
<212> TYPE: DNA
<213> ORGANISM: Oryza sativa

<400> SEQUENCE: 66
gtcaattgga ggccccttct cgttcgcacc                                    30

<210> SEQ ID NO 67
<211> LENGTH: 30
<212> TYPE: DNA
<213> ORGANISM: Oryza sativa

<400> SEQUENCE: 67
attgaaggtt gaaactagga agaactgtgc                                    30

<210> SEQ ID NO 68
<211> LENGTH: 30
<212> TYPE: DNA
<213> ORGANISM: Oryza sativa

<400> SEQUENCE: 68
tgcccgcgtg gacctggtag gccgtgccgc                                    30

<210> SEQ ID NO 69
<211> LENGTH: 30
<212> TYPE: DNA
<213> ORGANISM: Oryza sativa

<400> SEQUENCE: 69
ggggagaggg aaggagggtg ggccagcttg                                    30

<210> SEQ ID NO 70
<211> LENGTH: 30
<212> TYPE: DNA
<213> ORGANISM: Oryza sativa

<400> SEQUENCE: 70
cggaggggag aaaggagaaa agtgagccca                                    30

<210> SEQ ID NO 71
<211> LENGTH: 30
<212> TYPE: DNA
<213> ORGANISM: Oryza sativa

<400> SEQUENCE: 71
tccaggccca ggtatcggcc cggccccaca                                    30

<210> SEQ ID NO 72
<211> LENGTH: 30
<212> TYPE: DNA
<213> ORGANISM: Oryza sativa

<400> SEQUENCE: 72
atgaacagtg tcagggaggc aaaacagact                                    30

<210> SEQ ID NO 73
<211> LENGTH: 30
<212> TYPE: DNA
<213> ORGANISM: Oryza sativa

<400> SEQUENCE: 73
tagcaaggat tgacagactg agagctcttt                                    30
```

```
<210> SEQ ID NO 74
<211> LENGTH: 30
<212> TYPE: DNA
<213> ORGANISM: Oryza sativa

<400> SEQUENCE: 74
ctgtagggat tgatgaagag tgagctgata                                    30

<210> SEQ ID NO 75
<211> LENGTH: 30
<212> TYPE: DNA
<213> ORGANISM: Oryza sativa

<400> SEQUENCE: 75
gctacgatgc tgctcctgtc cgccccttga                                    30

<210> SEQ ID NO 76
<211> LENGTH: 30
<212> TYPE: DNA
<213> ORGANISM: Oryza sativa

<400> SEQUENCE: 76
ctctggccaa tggaacaatg taggcaaggg                                    30

<210> SEQ ID NO 77
<211> LENGTH: 30
<212> TYPE: DNA
<213> ORGANISM: Oryza sativa

<400> SEQUENCE: 77
gattaacgag attcccactg tccctgtcta                                    30

<210> SEQ ID NO 78
<211> LENGTH: 30
<212> TYPE: DNA
<213> ORGANISM: Oryza sativa

<400> SEQUENCE: 78
gtgacattgc tgctattgct ggaagtcccg                                    30

<210> SEQ ID NO 79
<211> LENGTH: 31
<212> TYPE: DNA
<213> ORGANISM: Oryza sativa

<400> SEQUENCE: 79
ccgccccgaa atcccgttgc ccccgacgga a                                  31

<210> SEQ ID NO 80
<211> LENGTH: 31
<212> TYPE: DNA
<213> ORGANISM: Oryza sativa

<400> SEQUENCE: 80 cccccctagcg aagaggccga gcaaaaatca g                                 31

<210> SEQ ID NO 81
<211> LENGTH: 31
<212> TYPE: DNA
<213> ORGANISM: Oryza sativa

<400> SEQUENCE: 81
gtgggtgggt gggtggtggt ggcccgccag g                                  31
```

```
<210> SEQ ID NO 82
<211> LENGTH: 31
<212> TYPE: DNA
<213> ORGANISM: Oryza sativa

<400> SEQUENCE: 82
ggcctgtcca actcatgctt gcctcccaat t                          31

<210> SEQ ID NO 83
<211> LENGTH: 21
<212> TYPE: DNA
<213> ORGANISM: Oryza sativa

<400> SEQUENCE: 83
cggcgggatc ggtggggaca c                                      21

<210> SEQ ID NO 84
<211> LENGTH: 11
<212> TYPE: DNA
<213> ORGANISM: Oryza sativa

<400> SEQUENCE: 84
ggtggggaca c                                                 11

<210> SEQ ID NO 85
<211> LENGTH: 21
<212> TYPE: DNA
<213> ORGANISM: Oryza sativa

<400> SEQUENCE: 85
gtcggccgag cggcgggatc g                                      21

<210> SEQ ID NO 86
<211> LENGTH: 11
<212> TYPE: DNA
<213> ORGANISM: Oryza sativa

<400> SEQUENCE: 86
gtcggccgag c                                                 11

<210> SEQ ID NO 87
<211> LENGTH: 10
<212> TYPE: DNA
<213> ORGANISM: Oryza sativa

<400> SEQUENCE: 87
ggcgggatcg                                                   10

<210> SEQ ID NO 88
<211> LENGTH: 10
<212> TYPE: DNA
<213> ORGANISM: Oryza sativa

<400> SEQUENCE: 88
gaagggacgc                                                   10

<210> SEQ ID NO 89
<211> LENGTH: 10
<212> TYPE: DNA
<213> ORGANISM: Oryza sativa

<400> SEQUENCE: 89
tgcacgtagc                                                   10
```

<210> SEQ ID NO 90
<211> LENGTH: 10
<212> TYPE: DNA
<213> ORGANISM: Oryza sativa

<400> SEQUENCE: 90
ggaggcggct                                                                10

<210> SEQ ID NO 91
<211> LENGTH: 10
<212> TYPE: DNA
<213> ORGANISM: Oryza sativa

<400> SEQUENCE: 91
actattcctt                                                                10

<210> SEQ ID NO 92
<211> LENGTH: 10
<212> TYPE: DNA
<213> ORGANISM: Oryza sativa

<400> SEQUENCE: 92
attcagtgga                                                                10

<210> SEQ ID NO 93
<211> LENGTH: 10
<212> TYPE: DNA
<213> ORGANISM: Oryza sativa

<400> SEQUENCE: 93
cctgcctcat                                                                10

<210> SEQ ID NO 94
<211> LENGTH: 10
<212> TYPE: DNA
<213> ORGANISM: Oryza sativa

<400> SEQUENCE: 94
acagacttta                                                                10

<210> SEQ ID NO 95
<211> LENGTH: 10
<212> TYPE: DNA
<213> ORGANISM: Oryza sativa

<400> SEQUENCE: 95
ggccccttct                                                                10

<210> SEQ ID NO 96
<211> LENGTH: 10
<212> TYPE: DNA
<213> ORGANISM: Oryza sativa

<400> SEQUENCE: 96
gctacgatgc                                                                10

<210> SEQ ID NO 97
<211> LENGTH: 10
<212> TYPE: DNA
<213> ORGANISM: Oryza sativa

<400> SEQUENCE: 97

```
atggaacaat                                                          10

<210> SEQ ID NO 98
<211> LENGTH: 10
<212> TYPE: DNA
<213> ORGANISM: Oryza sativa

<400> SEQUENCE: 98
gagattccca                                                          10

<210> SEQ ID NO 99
<211> LENGTH: 10
<212> TYPE: DNA
<213> ORGANISM: Oryza sativa

<400> SEQUENCE: 99
gttgatttgg                                                          10

<210> SEQ ID NO 100
<211> LENGTH: 10
<212> TYPE: DNA
<213> ORGANISM: Oryza sativa

<400> SEQUENCE: 100
attgctgcta                                                          10
```